United States Patent
Ptasznik et al.

(10) Patent No.: US 6,413,773 B1
(45) Date of Patent: *Jul. 2, 2002

(54) PHOSPHATIDYLINOSITOL 3-KINASE INHIBITORS AS STIMULATORS OF ENDOCRINE DIFFERENTIATION

(75) Inventors: Andrezej Ptasznik, Philadelphia, PA (US); Alberti Hayek, La Jolla; Gillian M. Beattie, Poway, both of CA (US)

(73) Assignee: The Regents of the University of California, Oakland, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/320,479

(22) Filed: May 26, 1999

Related U.S. Application Data

(60) Provisional application No. 60/087,730, filed on Jun. 2, 1998, and provisional application No. 60/087,558, filed on Jun. 1, 1998.

(51) Int. Cl.⁷ .......................... C12N 5/06; C12N 5/00; C12N 5/08
(52) U.S. Cl. ....................... 435/377; 375/366
(58) Field of Search ................. 435/366, 325, 435/377

(56) References Cited

U.S. PATENT DOCUMENTS

| | | | |
|---|---|---|---|
| 5,276,167 A | 1/1994 | Bhatnagar et al. ............ 549/302 |
| 5,378,725 A | * 1/1995 | Bonjouklian et al. ......... 514/453 |
| 5,468,773 A | * 11/1995 | Dodge et al. ................ 514/453 |
| 5,480,906 A | 1/1996 | Creemer et al. ............. 514/453 |
| 5,885,777 A | 3/1999 | Stoyanov et al. .............. 435/6 |

OTHER PUBLICATIONS

Gao et al. DIABETES. Jul. 1996. vol. 54, pp. 854–862.*
Aldridge et al. (1975) *J. Chem. Soc. Perkin Trans.* I: 943–945.
Alpert et al. (1988) *Cell.* 53:259–308.
Auger et al. (1989) *Cell*, 57:167–175.
Backer et al. (1993) *J. Biol. Cjem.* 268:8204–8212.
Beattie et al. (1994) *J. Clin. Endocrinol. Metab.* 78:1232–1240.
Beattie et al. (1996) *Diabetes.* 45:1223–1228.
Beattie et al. (1997) *Diabetes.* 46:244–248.
Brinkmann et al. (1995) *J. Cell Biol.* 131:1573–1586.
Busca et al. (1996) *J. Biol. Chem.* 271:31824–31830.
Carpenter and Cantley (1996) *Curr. Opin. Cell Biol.* 8:153–158.
Cordier–Bussat et al. (1995) *Mol. Cell. Biol.* 15:3904–3916.
De Tata et al. (1993) *Exp. Cell. Res.* 205:261–269.
Feber (1999) Science, 284:422–425.
Grove et al. (1965) *J. Chem. Soc.*, Jun.: 3803–3825.
Hanson et al. (1985) *J. Chem. Soc. Perkin Trans.* I: 1311–1314.
Harbeck et al. (1996) *Diabetes.* 45:711–717.
Hempstead et al. (1992) *Neuron.* 9:883–896.
Henderson and Stein (1994) *Mol. Cell. Biol.* 14:655–662.
Herrera et al. (1991) *Development (Camb.).* 113:1257–1265.
Hiles et al. (1992) *Cell.* 70:419–429.
Hu et al. (1993) *Mol. Cell. Biol.* 13:7677–7688.
Inagaki et al. (1992) *Proc. Natl. Acad. Sci. USA.* 89:1045–1049.
Jonsson et al. (1994) *Nature (Lond.)* 371:606–609.
Kimura et al. (1994) *J. Biol. Chem.* 269:18961–18967.
Koranyi et al. (1992) *J. Clin. Invest.* 89:432–436.
Kruse et al. (1993) *Genes Dev.* 7:774–786.
Leonardo and Baltimore (1989) *Cell.* 58:227–229.
Miller (1994) *EMBO J.* 13:1145–1156.
Nakanishi et al. (1993*J. Biol. Chem.* 268:13–16.
Newgard et al. (1995) *Annu. Rev. Biochem.* 64:689–719.
Oberg et al. (1994) *Growth Fact.* 10:115–126.
Philippe et al. (1987) *J. Clin. Invest.* 79:351–358.
Philippe et al. (1987) *Mol. Cell. Biol.* 7:560–563.
Ptasznik et al. (1996) *J. Biol. Chem.* 271:25204–25207.
Ptasznik et al. (1997) *J. Cell Biol.* 137(5): 1127–1136.
Pulverer et al. (1991) *Nature (Lond.)* 353:670–672.
Robertson (1992) *New England J. Med.*, 327:1861–1868.
Saad et al. (1994) *Mol. Endocrinol.* 8:545–557.
Sandler et al. (1985) *Diabetes.* 34:1113–1119.
Sandler et al. (1989) *Diabetes.* 38(Suppl1):168–171.
Stoyanov et al. (1995), *Science* 269:690–693.
Teitelman et al. (1987) *Dev. Biol.* 121:454–466.
Thomas et al. (1992) *Cell.* 68: 1031–1040.
Toker, et al. (1994) *J. Biol. Chem.* 269:32358–32367.
Tomasz et al. (1987) *Science (Wash. DC)* . 235:1204–1208.
Touhara et al. (1995) *Proc. Natl. Acad. Sci. USA.* 92: 9284–9287.
Vlahos, C.J. et al. (1994) *J. Biol., Chem.*, 269:5241–5248.
Watada et al. (1996) *Diabetes.* 45:1826–1831.
Whitman et al. (1988) *Nature*, 332: 644–646.
Yonemura et al. (1984) *Diabetes.* 33:401–405.

* cited by examiner

Primary Examiner—Sandra E. Saucier
Assistant Examiner—Vera Afremova
(74) Attorney, Agent, or Firm—Quine Intellectual Property Law Group P.C.; Tom Hunter

(57) ABSTRACT

This invention pertains to the discovery that inhibition of phosphatidylinositol 3-kinase (PI3K) in human fetal undifferentiated cells induces morphological and functional endocrine differentiation. This is associated with an increase in mRNA levels of insulin, glucagon, and somatostatin, as well as an increase in the insulin protein content and secretion response to secretagogues. Blockade of PI3K also increases the proportion of pluripotent precursor cells coexpressing multiple hormones and the total number of terminally differentiated cells originating from these precursor cells.

8 Claims, 8 Drawing Sheets

PHOSPHATIDYLINOSITOL 3-KINASE INHIBITORS AS STIMULATORS OF ENDOCRINE DIFFERENTIATION

CROSS-REFERENCE TO RELATED APPLICATIONS

This application claims benefit under 35 U.S.C. §119 of provisional patent application No. 60/087,558, filed on Jun. 1, 1998 and provisional patent application No. 60/087,730, filed on Jun. 2, 1998 both of which are incorporated by reference in their entirety for all purposes.

STATEMENT AS TO RIGHTS TO INVENTIONS MADE UNDER FEDERALLY SPONSORED RESEARCH AND DEVELOPMENT

[Not Applicable]

FIELD OF THE INVENTION

This invention relates to the field of cell culture and to the treatment of endocrine disorders. In particular, this invention pertains to methods of inducing endocrine differentiation in cell culture thereby providing endocrine cell suitable for transplantation into a host organism

BACKGROUND OF THE INVENTION

Many kinds of cells can be grown in culture, provided that suitable nutrients and other conditions for growth are supplied. Thus, since 1907 when Harrison noticed that nerve tissue explanted from frog embryos into dishes under clotted frog lymph developed axonal processes, scientists have made copious use of cultured tissues and cells from a variety of sources. Such cultures have been used to study genetic, physiological, and other phenomena, as well as to manufacture certain macromolecules using various fermentation techniques known in the art. In studies of mammalian cell biology, cell cultures derived from lymph nodes, muscle, connective tissue, kidney, dermis and other tissue sources have been used.

Generally speaking, the tissue sources that have been most susceptible to the preparation of cell cultures for studies are derivatives of the ancestor mesodermal cells of early development. Tissues that are the progeny of the ancestor endodermal and ectodermal cells have only in recent years become amenable to cell culture, of a limited sort only. The cell types derived from the endoderm and ectoderm of early development include epidermis, hair, nails, brain, nervous system, inner lining of the digestive tract, various glands, and others. Essentially, long-term cultures of normal differentiated glandular and epithelial cells, particularly those from humans, are still not available.

In the instance of the mammalian pancreas, until the present invention, no scientist has had the opportunity of studying, and no physician has had the prospect of using for treatment, a cell culture of pancreatic endocrine cells that exhibited sustained cell division and the glandular properties typical of the pancreas.

Similar to neurons, the endocrine cells of the mammalian pancreas have been considered to be post-mitotic, i.e., terminal, essentially non-dividing cells. Recent work has shown that the cells of the mammalian pancreas (including those of humans) are capable of survival in culture, however, propagation of differentiated (mature) cells having endocrine function has met with, at best, limited success.

The inability to study pancreatic endocrine cells in culture has impeded the ability of medical science to progress in the area of pancreatic disorders. Such disorders include diabetes mellitus, a disease that impairs or destroys the ability of the beta cells of the islets of Langerhans (structures within the pancreas) to produce sufficient quantities of the hormone insulin, a hormone that serves to prevent accumulation of sugar in the bloodstream. Type I diabetes mellitus (insulin dependent, or juvenile-onset diabetes) typically requires full hormone replacement therapy. In a second (and more common) form of the disease, type II diabetes (sometimes referred to as late onset, or senile diabetes), treatment often does not require insulin injections because a patient suffering with Type II diabetes may be able to control his/her blood sugar levels by carefully controlling food intake. However, as many as 30% of these patients also have reduced beta cell function and therefore are candidates for hormone replacement therapy as well. Diabetes is not confined to humans, but has been noted in other mammals as well, such as dogs and horses.

The etiology of the diabetic disease condition is not fully understood. However, it has been noted that autoimmunity antibodies (antibodies that "mistakenly" attack bodily structures) and/or certain T lymphocytes may have an involvement long before clinical symptoms of diabetes emerge. Evidence in this direction relies, in part, on successful treatment of recently diagnosed diabetic patients with cyclosporin, an immunosuppressive drug. Such treatment has been shown to prevent or cause remission of insulin-dependent diabetes mellitus in mice (Mori et al. (1986) *Diabetologia* 29:244–247), rats (Jaworski et al. (1986) *Diabetes Res.* 3:1–6), and humans (Feutren et al. (1986) *Lancet*, 11:119–123). A clinical test to detect the presence of these humoral and cellular immunoreactions would allow the screening of individuals in a pre-diabetic state, which individuals could then be prophylactically treated with immunosuppressive drugs.

Current treatment of individuals with clinical manifestation of diabetes attempts to emulate the role of the pancreatic beta cells in a non-diabetic individual. Individuals with normal beta cell function have tight regulation of the amount of insulin secreted into their bloodstream. This regulation is due to a feed-back mechanism that resides in the beta cells that ordinarily prevents surges of blood sugar outside of the normal limits. Unless blood sugar is controlled properly, dangerous, even fatal, levels can result. Hence, treatment of a diabetic individual involves the use of injected bovine, porcine, or cloned human insulin on a daily basis.

Injected insulin and diet regulation permit survival and in many cases a good quality of life for years after onset of the disease. However, there is often a gradual decline in the health of diabetics that has been attributed to damage to the vascular system due to the inevitable surges (both high and low) in the concentration of glucose in the blood of diabetic patients. In short, diabetics treated with injected insulin cannot adjust their intake of carbohydrates and injection of insulin with sufficient precision of quantity and timing to prevent temporary surges of glucose outside of normal limits. These surges are believed to result in various vascular disorders that impair normal sight, kidney, and even ambulatory functions.

Both of these disease states, i.e., type I and type II diabetes, involving millions of people in the United States alone, preferably should be treated in a more regulated fashion. Successful transplants of whole isolated islets, for example, have been made in animals and in humans. However, long term resolution of diabetic symptoms has not yet been achieved by this method because of a lack of persistent functioning of the grafted islets in situ (see Robertson (1992) *New England J. Med.*, 327:1861–1863).

For the grafts accomplished thus far in humans, one or two donated pancreases per patient treated are required. Unfortunately only some 6000 donated human pancreases become available in the United States in a year, and many of these are needed for whole pancreas organ transplants (used when the pancreas has been removed, usually during cancer surgery). Therefore, of the millions of diabetic individuals who could benefit from such grafts, only a relative handful of them may be treated given the current state of technology. If the supply of islet cells (including but not necessarily limited to beta cells) could be augmented by culturing the donated islets in cell culture, expanded populations would provide sufficient material to allow a new treatment for insulin-dependent diabetes.

SUMMARY OF THE INVENTION

This invention provides methods of culturing cells that differentiate and provide cells having endocrine activity in vitro. The methods generally involve culturing the cells in the presence of a phosphatidylinositol 3-kinase (PI3K) inhibitor. By using a PI3K inhibitors in the culture media, the ratio of endocrine positive (i.e. hormone producing and/or secreting cells) to endocrine negative cells is dramatically increased. Preferred mammalian cells include endocrine precursor cells, more preferably pancreas endocrine precursor cells (e.g. cells capable of differentiating into pancreas endocrine cells). Particularly preferred cells are pancreas cells (adult or fetal), more preferably human pancreas cells. Suitable phosphatidylinositol 3-kinase inhibitors include, but are not limited to wortmannin, a wortmannin analogue, Ly294002, and a Ly294002 analogue.

These culture methods thus provide a means by which large quantities of previously unavailable endocrine positive cells can be obtained. These cells find a number of uses, for example in the treatment of conditions characterized by a hormone deficiency (e.g. diabetes). Thus in another embodiment, this invention provides methods of treating a hormone deficiency in an organism, particularly a hormone deficiency characterized by a deficiency in insulin and/or glucagon, and/or somatostatin. The methods involve culturing a mammalian precursor cell in the presence of a phosphatidylinositol 3-kinase (PI3K) inhibitor whereby said precursor cell differentiates into a cell having endocrine activity; and then transplanting the cell having endocrine activity into said organism. The precursor cell can be virtually any endocrine precursor cell and more preferably is a pancreatic cell (e.g. a β-cell). The method is particular well suited for treating conditions characterized by insulin deficiency (e.g. diabetes).

In another embodiment, this invention provides nutrient media suitable for the culture of differentiated mammalian cells having endocrine activity. In a preferred embodiment, the nutrient medium comprises a mammalian cell culture medium and a phosphatidylinositol 3-kinase inhibitor. Preferred inhibitors include, but are not limited to wortmannin, a wortmannin analogue, Ly294002, or a Ly294002 analogue and preferred culture media include, but are not limited to Eagle's Basal Medium (BME), Eagle's Minimum Essential Medium (MEM), Minimum Essential Medium with Non-Essential Amino Acids (MEM/NEAA), Dulbecco's Modification of Eagle's Medium (DMEM), McCoy's 5 A, and Rosewell Park Memorial Institute (RPMI).

In still another embodiment, this invention provides a bioreactor. The bioreactor comprises a container containing a nutrient medium as described herein and a mammalian precursor cell capable of endocrine activity when differentiated.

Kits are also provided for the in vitro culture of differentiated endocrine cell(s). In a preferred embodiment, the kits comprise a container containing a phosphatidylinositol 3-kinase (PI3K) inhibitor and one or more other components selected from t5eh group consisting of a cell culture medium, adult mammalian cells, fetal mammalian cells, undifferentiated mammalian cells, partially differentiated mammalian cells, and/or instructional materials teaching the use of PI3K inhibitors to enhance the differentiation of endocrine cells in culture.

DEFINITIONS

The following abbreviations are used herein: HGF/SF, hepatocyte growth factor/scatter factor; ICC, islet-like cell cluster; NIC, nicotinamide; PI3K, phosphatidylinositol 3-kinase; PI, phosphatidylinositol; PIP, phosphatidylinositol 4 phosphate; PIP2, phosphatidylinositol 4,5 bisphosphate; PIP3 or PtdIns(3,4,5)P3, phosphatidylinositol 3,4,5 trisphosphate; PKC, protein kinase C; PtdIns(3)P, phosphatidylinositol 3 phosphate; PtdIns(3,4)P2, phosphatidylinositol 3,4 bisphosphate.

The term "differentiation" refers to the process whereby cells or cell clones assume specialized functional biochemistries and/or morphologies previously absent. Such "determined" cells may lose the ability to divide. Typically differentiation of a cell into one type of cell limits or prevents differentiation of a cell into another type. Differentiation of endocrine cells is characterized by the ability to express and/or secrete one or more hormones.

The term "culture medium", refers to a chemical composition that supports the growth and/or proliferation of a cell, preferably of a mammalian cell. Typical culture media include suitable nutrients (e.g. sugars, amino acids, proteins, and the like) to support the growth and/or proliferation of a cell. Media for the culture of mammalian cells are well known to those of skill in the art are include, but are not limited to Medium 199, Eagle's Basal Medium (BME), Eagle's Minimum Essential Medium (MEM), Minimum Essential Medium with Non-Essential Amino Acids (MEM/NEAA), Dulbecco's Modification of Eagle's Medium (DMEM), McCoy's 5A, Rosewell Park Memorial Institute (RPMI) 1640, modified McCoy's 5A, Ham's F10 and F12, CMRL 1066 and CMRL 1969, Fisher's medium, Glasgow Minimum Essential Medium (GMEM), Iscove's Modified Dulbecco's Medium (IMDM), Leibovitz's L-15 Medium, McCoy's 5A medium, S-MEM, NCTC-109, NCTC-135, Waymouth's MB 752/1 medium, Williams' Medium E, and the like. Cell culture media are commercially available (e.g. from GibcoBRL, Gaithersburg, Md.) and even custom-developed culture media are commercially available (see, e.g., Specialty Media, Cell and Molecular Technologies, Inc., Phillipsburg, N.J.).

The term "endocrine activity" as used herein refers to the activity of a cell in producing (expressing) and/or secreting a hormone (e.g. insulin, glucagon, etc.).

The terms "precursor cell" or "endocrine precursor cell" as used herein refer to a cell that is capable of ultimately differentiating into a mature endocrine cell (e.g. a cell that produces (expresses) and/or secretes a hormone) under suitable conditions (in vitro and/or in vivo).

The term "Ly294002", as used herein, refers to the phosphatidylinositol 3-kinase inhibitor, 2-(4-Morpholinyl)-8-phenyl-4 H-1-benzopyran-4-one; as described by Vlahos, et al. (1994) *J. Biol., Chem.*, 269(7) 5241–5248, and is available from Calbiochem Corp., La Jolla Calif.

Phosphatidylinositol (PI) 3'-kinase (Kazlauskas and Cooper (1989) *Cell* 58: 1121; Coughlin et al. (1989) *Science*

243, 1191) refers to a compound or compounds that phosphorylate the inositol ring of PI in the D-3 position (Whitman et al (1988) *Nature* 332, 644). PI3K activity is associated with a variety of activated tyrosine kinases and correlates with the presence of a tyrosine phosphorylated 85-kilodalton (kD) protein (p85) (Kaplan et al. (1987) *Cell* 50: 1021; Fukui and Hanafusa (1989) *Mol. Cell. Biol.* 9, 1651). Purified PI3K is a heterodimeric complex that contains p85 and a 110-Kd protein (p110) (Carpenter et al. (1990) *J. Biol. Chem.* 265, 19704). The purified p85 subunit has no detectable PI3K activity, but binds tightly to activated PDGFR or EGFR in vitro. PDGF stimulation induces accumulation of PI-3,4-P$_2$ and PI-3,4,5-P$_3$, confirming that PI3K is regulated by tyrosine kinases in vivo. Phosphatidylinositol-kinases belong, together with specific phospholipases, to an enzyme group which catalyses the formation of intracellular messenger substances from the membrane lipid phosphatidyl inositol (PI).

BRIEF DESCRIPTION OF THE DRAWINGS

[FIG. 1A] glucagon, insulin, cyclophilin; [FIG. 1B] somatostatin, cyclophilin); M, RNA molecular size markers, in nucleotides (Ambion, Inc., Austin, Tex.). FIG. 1C shows quantitative analysis of hormone transcription levels. Densitometrically determined band intensities of target mRNAs are shown after normalization to the cyclophilin signal from the RNase protection assays shown in FIGS. 1A and 1B. Values are compared to the control samples. Results shown are representative of two independent experiments.

FIG. 4A shows the effect of PI3K inhibitors on [$^3$H]thymidine incorporation into DNA. ICCs were cultured as described in FIG. 2. [$^3$H]thymidine (1 mCi/ml) was added to the cultures 16 h before the assay. Data are combined from three independent experiments and are presented as percentage of control ICCs from each experiment. (Absolute control values were 2086±172, 4552±583, and 7625±536 cpm/mg DNA). *P<0.05 compared to control, **P<0.05 compared to treatment with nicotinamide or wortmannin. Inhibition of DNA synthesis by mitomycin C or serum starvation does not affect insulin protein expression in fetal ICCs. ICCs were cultured in the presence of 2 mg/ml mitomycin C for 5 d (FIG. 4B) or starved in 0.5% FBS for 2 d (FIG. 4C). Subsequently, [$^3$H]thymidine incorporation and insulin protein content were measured as described in Materials and Methods.

FIG. 6A shows an autoradiogram of a thin layer chromatographic separation of cell phospholipids showing levels of PIP3 in fetal islet cells treated continuously for 5 d in the absence (Cont) or presence of 25 ng/ml HGF/SF (HGF) or 10 mM nicotinamide (NIC). FIG. 6B show the quantification of radioactivity in PIP3 spots expressed relative to control. Results shown are representative of three similar experiments. PA, phosphatidic acid; PC, phosphatidylcholine.

DETAILED DESCRIPTION

Figure 1A:
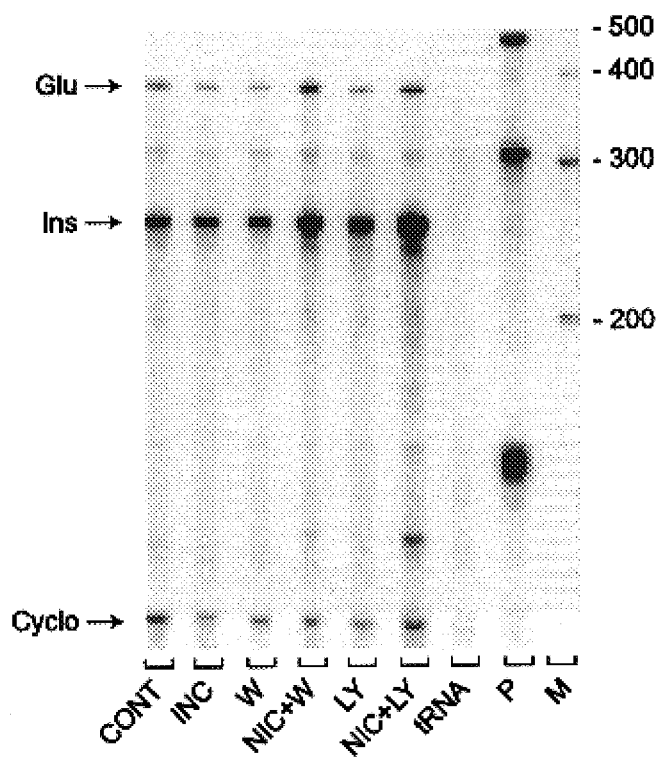
FIGS. 1A, 1B, and 1C show the stimulatory effect of PI3K inhibitors on islet hormone gene expression. Total RNA from ICCs cultured for 5 d was hybridized simultaneously to radiolabeled antisense riboprobes for (FIG. 1A) glucagon (Glu), insulin (Ins), and cyclophilin (Cyclo), or (FIG. 1B) somatostatin (Som) and cyclophilin (Cyclo). Protected fragments for glucagon (389 nucleotides), insulin (262 nucleotides), somatostatin (206 nucleotides), and cyclophilin (135 nucleotides) are indicated. Lanes: CONT, control ICCs; NIC, W, and LY, ICCs cultured in the presence of nicotinamide, wortmannin, or Ly294002, respectively; NIC1W or NIC1LY, ICCs cultured in the presence of the combination of nicotinamide and either wortmannin or Ly294002; tRNA, yeast tRNA (10 mg) used as a negative control; P, mixture of undigested probes (from top.

This invention pertains to the discovery of a previously unrecognized function for phosphatidylinositol 3 kinase (PI3K) as a negative regulator of endocrine-specific gene expression in human cells. While the process of endocrine differentiation has been extensively studied, no specific intracellular signaling pathway directly involved in regulating expression of endocrine-specific genes has been previously identified.

In particular, it was a discovery of this invention that the partial or complete blockade of PI3K activity in human fetal (and adult) undifferentiated cells induces morphological and functional endocrine differentiation in vitro. This is associated with an increase in mRNA levels of insulin, glucagon, and somatostatin, as well as an increase in insulin protein content and secretion in response to seretagogues. Blockade of PI3K activity also increased the proportion of pluripotent precursor cells coexpressing multiple hormones and the total number of mature endocrine cells originating from these precursor cells.

The inhibition of PI3K activity thus provides a means of inducing the maturation (differentiation) of cells having endocrine activity in vitro. Using PI3K inhibitors in culture, one can readily prepare large numbers of essentially pure cells that have a number of uses including, but not limited to use as a source of secreted hormones, use as subjects for investigation of signaling in endocrine cells, and as subjects for transplantation into host organisms (e.g. mammals such as largomorphs, rodents, bovines, canines, felines, primates including humans, etc.), and in the treatment of pathological conditions characterized by a hormone deficiency.

In one particular preferred embodiment, this invention utilizes PI3K inhibitors to culture human pancreas cells that differentiate and show endocrine activity (i.e., secrete one or more hormones), in particular to culture human pancreas cells that secrete insulin.

I. Isolation and Culture of Cells.

This invention pertains to the use of PI3K inhibitors to induce differentiation of precursor cells into differentiated cells having endocrine activity. The methods of this invention involve culturing mammalian cells in the presence of one or more PI3K inhibitor(s). The cells are otherwise cultured according to standard methods well known to those of skill in the art. Preferred culture conditions are illustrated in Example 1.

Virtually any mammalian cell can be used in the methods of this invention, however preferred cells are those that are generally known to ultimately differentiate into an endocrine tissue under normal (healthy) conditions. The cells can be totipotent or pluripotent or can be cells whose fate is further determined.

Suitable pre-endocrine cells (precursor) cells of this invention include, but are not limited to cells that differentiate into pancreatic cells such as α cells, β cells, delta cells, and pancreatic polypeptide cells. The cells can be obtained from pancreatic tissue or from other tissues (e.g. embryonic brain cells) that are totipotent or pluripotent and that can be induced to differentiate into endocrine cells.

It will be recognized that it is not necessary to isolate the particular "precursor" cells prior to culture. To the contrary, suitable populations of cells can be obtained simply by homogenizing an organ or tissue generally recognized as containing one or more of such cells.

In one embodiment, the pancreas cells (fetal or adult) from human or other mammalian subjects, are provided by digestion, e.g. with collagenase P, of pancreases followed by tissue culture. It was noted that after 5 days of culture, islet-like cell clusters (ICCs) formed. Endocrine cells developing within ICCs originated from undifferentiated, pluripotent epithelial cells and contained insulin-producing β-cells and three other cell types, α, δ, and pp, secreting glucagon, somatostatin, and pancreatic polypeptide respectively. The cells cultured for 5 days are preferably treated with LY294002 (10 $\mu$M) (Calbiochem Corp., La Jolla Calif.) or wortmannin (Sigma Chemical Col., St. Louis, Mo.)(100 nM).

The continuous blockade of PI3K activity by these drugs increased the number of hormone producing cells growing in ICCs. Ly294002-induced increase in hormone expression was much more pronounced. Without being bound to a particular theory, it is believed that wortmannin is a less stable agent than Ly294002 in culture medium.

In addition to cells derived directly from various organs or tissues, it is also possible to utilize cultured cells, e.g. various cell lines. Cell lines suitable for practice of this invention include, but are not limited to pancreatic endocrine cell lines derived from human fetal or adult islets and endocrine cell precursors. Pancreas-derived cell lines are well known to those of skill in the art (see, e.g., ATCC CRL-1837, ATCC CRL-1997, etc.).

While one preferred set of culture conditions is illustrated in Example 1, other culture conditions are suitable as well. Generally, culture conditions typical for mammalian cell or tissue culture are acceptable. Mammalian cell and tissue culture methods are well known to those of skill in the art (see, e.g., Freshney et al. (1994) *Culture of Animal Cells, a Manual of Basic Technique, third edition* Wiley-Liss, New York) and the references cited therein for a discussion of how to isolate and culture cells).

The phosphatidylinositol 3-kinase inhibitor concentration in culture ranges from about 10 nM to about 100 $\mu$M, preferably from about 20 nM to about 50 $\mu$M, more preferably from about 20 nM to about 10 $\mu$M. The phosphatidylinositol 3-kinase inhibitor concentration can be optimized for any cell type/culture media combination. Such optimization simply involves culturing the particular cells of interest in a particular medium at a range of different phosphatidylinositol 3-kinase inhibitor concentrations and then assaying the resulting cells for endocrine activity or another indicator of differentiation, e.g., as described below.

II. Phosphatidylinositol 3 Kinase (PI3K) Inhibitors.

A) Known Phosphatidylinositol 3 Kinase Inhibitors.

Phosphatidylinositol 3-kinase inhibitor are well know to those of skill in the art. Such inhibitors include, but are not limited to Ly294002 (Calbiochem Corp., La Jolla, Calif.) and wortmannin (Sigma Chemical Co., St. Louis Mo.) which are both potent and specific PI3K inhibitors. The chemical properties of Ly294002 are described in detail in *J. Biol., Chem.*, (1994) 269: 5241–5248. Briefly, Ly294002, the quercetin derivative, was shown to inhibit phosphatidylinositol 3-kinase inhibitor by competing for phosphatidylinositol 3-kinase binding of ATP. At concentrations at which Ly294002 fully inhibits the ATP-binding site of PI3K, it has no inhibitory effect against a number of other ATP-requiring enzymes including PI4-kinase, EGF receptor tyrosine kinase, src-like kinases, MAP kinase, protein kinase A, protein kinase C, and ATPase.

According to the data presented herein, Ly294002 is the most potent factor that has ever been reported to induce β-cell differentiation to date. Ly294002 is very stable in tissue culture medium, is membrane permeable, has no significant cytotoxicity, and at concentrations at which it inhibits members of PI3K family, it has no effect on other signaling molecules.

B) Other PI3K Inhibitors.

Phosphatidylinositol 3-kinase, has been found to phosphorylate the 3-position of the inositol ring of phosphatidylinositol (PI) to form phosphatidylinositol 3-phosphate (PI-3P) (Whitman et al.(1988) *Nature*, 322: 664–646). In addition to PI, this enzyme also can phosphorylate phosphatidylinositol 4-phosphate and phosphatidylinositol 4,5-bisphosphate to produce phosphatidylinositol 3,4-bisphosphate and phosphatidylinositol 3,4,5-trisphosphate (PIP3), respectively (Auger et al. (1989) *Cell*, 57: 167–175). PI3K inhibitors are materials that reduce or eliminate either or both of these activities of P3 K.

1) Preparation of Other Inhibitors.

Numerous inhibitors of PI3K and their analogues are known. These include, but are not limited to viridin, viridiol, demethoxyviridin, and demethoxyviridiol (see, U.S. Pat. No. 5,276,167). Once viridin, viridiol, demethoxyviridin, and demethoxyviridiol, or other PI3K inhibitors are isolated and purified, analogs of each may be prepared via well known methods to provide generally known compounds such as those illustrated by formula I of U.S. Pat. No. 5,276,167 (see, also, Grove et al. (1965) *J. Chem. Soc.*, June: 3803–3811, Hanson et al. (1985) *J. Chem. Soc. Perkin Trans.* I: 1311–1314. Aldridge et al. (1975) *J. Chem. Soc. Perkin Trans.* I: 943–945 (1975), and Blight et al. *J. Chem. Soc. Perkin Trans I*: 1317–1322). Generally, the $R^1$ position hydroxy functionality of each of the formula I compounds of U.S. Pat. No. 5,276,167 may be acetylated, alkylated, oxidized, or dehydrated and alkylated. Similarly, the $R^2$ functionality (=O) of each of the named formula I compounds of U.S. Pat. No. 5,276,167 may be alkylated, or reduced to form an alcohol. The $R^3$ functionality of formula I compounds of U.S. Pat. No. 5,276,167, when $R^3$ is =O, also may be alkylated to form an acetyl group.

In addition, the alcohol of virone (formula II of U.S. Pat. No. 5,276,167 in which $R^3$, is =O) may be prepared via known procedures, and analogs of wortmannolone (formula III in which $R^2$, is =O and $R^3$, is —OH) may be prepared via either reduction of the R2' functionality, oxidation of the $R^3$ functionality, or both, using well known procedures.

Suitable derivatives and analogues include, but are not limited to alpha/beta-viridin, 1-acetylviridin, 1-methylether of viridin, demethoxyviridin, demethoxyviridin monoacetate, dehydroxyviridin, demethoxyviridin monomethanesulfonate, diacetyldemethoxyviridol OAc, viridiol, 1-O-acetylviridiol, 1-O-methyl-methylether of viridiol, demethoxyviridiol, 1-acetyldemethoxyviridiol, 1-O-methylether dimethoxyviridiol (see, U.S. Pat. No. 5,276, 167).

Other derivatives include, but are not limited to Wortmannin stereochemical alcohol and ester derivatives, such as 11-substituted, 17-substituted and 11, 17 disubstituted derivatives of wortmannin (see, U.S. Pat. No. 5,480,906), and the like.

2) Combinatorial Chemical Libraries

Other inhibitors can be identified from combinatorial libraries by the use of high-through put screens. A combinatorial chemical library is a collection of diverse chemical compounds generated by either chemical synthesis or biological synthesis by combining a number of chemical "building blocks" such as reagents. For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) 37(9): 1233–1250).

Preparation and screening of combinatorial chemical libraries is well known to those of skill in the art. Such combinatorial chemical libraries include, but are not limited to, peptide libraries (see, e.g., U.S. Pat. No. 5,010,175, Furka (1991) *Int. J. Pept. Prot. Res.*, 37: 487–493, Houghton et al. (1991) *Nature*, 354: 84–88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, Dec. 26, 1991), encoded peptides (PCT Publication WO 93/20242, Oct. 14, 1993), random bio-oligomers (PCT Publication WO 92/00091, Jan. 9, 1992), benzodiazepines (U.S. Pat. No. 5,288,514), diversomers such as hydantoins, benzodiazepines and dipeptides (Hobbs et al., (1993) *Proc. Nat. Acad. Sci. USA* 90: 6909–6913), vinylogous polypeptides (Hagihara et al. (1992) *J. Amer. Chem. Soc.* 114: 6568), nonpeptidal peptidomimetics with a β-D-Glucose scaffolding (Hirschmann et al., (1992) *J. Amer. Chem. Soc.* 114: 9217–9218), analogous organic syntheses of small compound libraries (Chen et al. (1994) *J. Amer. Chem. Soc.* 116: 2661), oligocarbamates (Cho, et al., (1993) *Science* 261:1303), and/or peptidyl phosphonates (Campbell et al., (1994) *J. Org. Chem.* 59: 658). See, generally, Gordon et al., (1994) *J. Med. Chem.* 37:1385, nucleic acid libraries (see, e.g., Strategene, Corp.), peptide nucleic acid libraries (see, e.g., U.S. Pat. No. 5,539, 083) antibody libraries (see, e.g., Vaughn et al. (1996) *Nature Biotechnology*, 14(3): 309–314), and PCT/US96/ 10287), carbohydrate libraries (see, e.g., Liang et al. (1996) *Science*, 274: 1520–1522, and U.S. Pat. No. 5,593,853), and small organic molecule libraries (see, e.g., benzodiazepines, Baum (1993) *C&EN*, January 18, page 33, isoprenoids U.S. Pat. No. 5,569,588, thiazolidinones and metathiazanones U.S. Pat. No. 5,549,974, pyrrolidines U.S. Pat. Nos. 5,525, 735 and 5,519,134, morpholino compounds U.S. Pat. No. 5,506,337, benzodiazepines U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433 A Applied Biosystems, Foster City, Calif., 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett_Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3 D Pharmaceuticals, Exton, Pa., Martek Biosciences, Columbia, Md., etc.).

3) Assays for Inhibitor Activity.

Methods of assaying for the activity of a putative PI3K inhibitor are well known to those of skill in the art. In general, the assays involve comparing the activity of PI3K (e.g. synthetic, recombinantly expressed, or purified PI3K) in the presence and absence of the putative PI3K inhibitor. Such assays are described in detail in U.S. Pat. No. 5,480,906. Briefly, PI 3-kinase activity is measured as described by Matter et al. (1992) *Biochem. Biophys. Res. Comm.*, 186: 624–631. Inhibitor candidates are initially dissolved, e.g., in DMSO and then diluted e.g., 10-fold with 50 mM of HEPES buffer, pH 7.5, containing 15 mM of $MgCl_2$ and 1 mM of EGTA. Ten microliters of this solution are incubated with purified PI 3-kinase (e.g., purified bovine brain PI3-kinase) (9 mu L) and phosphatidylinositol (5 mu L of a 2 mg/mL stock solution in 50 mM of HEPES buffer, pH 7.5, containing 1 mM of EGTA). The final reaction mixture contained 0.1–5 ng/mL of inhibitor and 3% of DMSO (v:v). This concentration of DMSO has no effect on PI3K activity. Control reaction mixtures contain 3% of DMSO (v:v) without inhibitor.

Reactants are preincubated 10 minutes at ambient temperature and then the enzyme reaction is started upon addition of 1 mu L [$^{32}$P] ATP (2 mCi/mL, 500 mu M of stock solution; 0.08 mCi/mL, 20 mu M of final concentration; Dupont New England Nuclear, Boston, Mass.). The reaction is allowed to proceed for 10 minutes at ambient temperature with frequent mixing, after which time the reaction is quenched by addition of 40 mu L of 1N HCl. Lipids are extracted with addition of 80 mu L $CHCl_3$:MeOH (1:1, v:v). The samples were mixed and centrifuged, and the lower organic phase is applied to a silica gel TLC plate (EM Science, Gibbstown, N.J.), which is developed in $CHCl_3$:MeOH:$H_2O$:$NH_4OH$ (45:35:8.5:1.5, v:v). Plates are dried, and the kinase reaction visualized by autoradiography. The phosphatidylinositol 3-monophosphate region is scraped from the plate and quantitated using liquid scintillation spectroscopy with ReadyProtein (Beckman Instruments, Inc., Fullerton, Calif.) used as the scintillation cocktail. The level of inhibition for the putative inhibitor (e.g. wortmann or Ly294002 analogues) is determined as the percentage of [$^{32}$P]-counts per minute compared to controls.

Alternatively, products of the PI3K reaction are confirmed by HPLC as discussed by Whitman (1988) *Nature*, 332:644–646. Phospholipids are deacylated in methylamine reagent and separated using a Whatman Partisphere SAX anion exchange column as previously described by Auger (1989) *Cell*, 57:167–175. A radio activity detector (e.g., Radiomatic Model A-140 Flo-One/Beta on-line radioactivity detector) is used to monitor the deacylated [$^{32}$P]-enzyme products. Deacylated [$^3$H]PI4-monophosphate is added as an internal standard.

4) Optimization of Inhibitor Dosages.

III. Treatment of Disease States.

A) Diabetes.

To date, the β-cell loss in insulin-dependent diabetes is terminal and cannot be reversed by regeneration of islets. The transplantation of islet cells offers an alternative therapy that can eliminate the requirement for exogenous insulin injections. Generally the methods involve engrafting functioning islet cells into an existing pancreas in a subject organism. Numerous approaches are known for engraftment. Where the islet cells are derived from the subject organism or a clone of that organism (e.g. an identical twin), or from an immunologically close relative, naked islet cells can be engrafted into the host pancreas.

Where the replacement β-cells are not closely related to the host, in a preferred embodiment, it is immunologically isolate the graft or to otherwise suppress immune rejection of the graft. In one embodiment, the cells are provided in implantable capsules that immunologically isolate the cells from the host organism. The capsules are typically designed with membranous walls that allow passage of nutrients into the capsule and allow escape of the secreted hormone. Such devices are well known to those of skill in the art are described, for example, in U.S. Pat. No. 5,738,673.

In another approach, the transplanted islet cells (or other differentiated endocrine cells) can be combined with sertoli cells to provide an immunologically privileged site (see, e.g., U.S. Pat. No. 5,725,854). Sertoli cells, which are the predominant cells of male testes can be separated from other testicular cells such as Leydig cells, peritubular cells and germ cells by conventional techniques. For example, the testes of a male mammal, such as a boar or ram, are first collected by castration. The testes are then chopped into several pieces and subsequently washed by centrifugation. Testicular Leydig cells can be removed from the tissue suspension using digestion agents such as trypsin and DNase. The remaining cell suspension is then washed by centrifugation several times. The pellet is resuspended in collagenase, incubated and washed by centrifugation to eliminate peritubular cells within the testes. Testicular germ cells can be removed by incubating the pellet with hyaluronidase and DNase. After several washings by centrifugation, the Sertoli cells can be collected to transplant using the method of the present invention.

The endocrine cells differentiated according to the methods of this invention may be co-cultured with Sertoli cells in tissue culture. Cells grown in tissue culture can be transplanted into a mammal in conjunction with the Sertoli cells as described in U.S. Pat. No. 5,725,854. The sertoli cells are administered in an amount effective to provide an immunologically privileged site. Such an effective amount is defined as that which prevents immune rejection of the subsequently or co-administered cells that produce the biological factor. Immune rejection can be determined for example histologically, or by functional assessment of the factor produced by the cells.

The cells used in the treatments of this invention can be stored using a variety of conventional techniques, such as cryopreserving the cells prior to growth in tissue culture for subsequent transplantation. It has been observed invention, that Sertoli cells co-cultured with endocrine cells such as islet cells enhance the proliferation and recovery rate of the factor producing cells in tissue culture and in particular, enhance the recovery rate and proliferation of factor producing cells that have been previously stored using techniques such as cryopreservation.

The differentiated endocrine and/or Sertoli cells can be from the same species as the mammal to be treated or from a different species. Further, the Sertoli cells and the endocrine cells need not be derived from the same species. It has been demonstrated that Sertoli cells from pigs in conjunction with islet of Langerhans from pigs can be used in the treatment of diabetes mellitus in rats. In a preferred embodiment the Sertoli cells are bovine, porcine non-human primate, or human.

B) Other Endocrine Disorders.

The data presented herein show that Ly294002 stimulates both endocrine cell mass and function in vitro. Moreover, the data indicate that PI3K inhibitors (e.g. Ly294002) induce endocrine differentiation and synthesis of, at least, three hormones (insulin, glucagon, and somatostatin) in human hormone precursor cells. This suggests that the described mechanism is a general phenomenon and is relevant in a variety of hormone-deficient states.

Thus, this invention contemplates the use of the above-described methods to treat virtually any disorder characterized by a hormone deficiency. As indicated above, such methods will comprise transplanting endocrine cells differentiated in culture in the presence of a PI3K inhibitor into an organism having the hormone deficiency. Endocrine cells will be used that express the hormone for which a deficiency exists. The cells can be encapsulated, naked, or administered with sertoli, or other cells as described above.

C) Creation of Synthetic Organs.

In still another embodiment, the differentiated endocrine cells produced according to the methods of this invention can be provided in the form of an artificial tissue or organ. In one variation, the artificial tissue/organ is produced by encapsulating the cells in a membrane or other container designed to permit the efflux of the desired hormone(s) and the influx of blood/plasma, or various nutrients as required. Semi-permeable membranes and other encapsulation devices suitable for such use are well known to those of skill in the art (see, e.g. U.S. Pat. No. 4,431,428).

In another embodiment, the cells can be cultured in a manner that they form actual tissues or organs. Means of growing tissues or organs in vitro are known to those of skill in the art (see, e.g., U.S. Pat. Nos. 4,431,428, 5,750,329, 5,695,996, 5,236,447, 4,925,555, 4,911,717.

U.S. Pat. Nos. 4,634,447, 4,643,715 and references therein). Typically this involves culturing the desired cells on a three-dimensional "scaffold". Preferred "scaffolds" are formed of biodegradable polymers, particularly branched or spongiform biodegradable plastics (e.g. branched and/or porous polyglycolic acid, polyglycolic acid/polylactide-coglycolide grafts, hydrolyzed polyclycolic acid polymers, etc.).

The "scaffold" provides three-dimensional organization for the cells comprising the artificial organ. once the organ is complete, particularly after implantation, the scaffold material is gradually resorbed leaving the totally biological organ.

It will be appreciated that while, in a preferred embodiment, the artificial organ is implanted within the body of the subject (e.g. intraperitoneally or subcutaneously), in other embodiments, the cells or artificial tissues/organs, can be contained in a bioreactor external to the organism and the desired hormone(s) can be delivered from the external source, e.g. via a catheter).

IV. Kits for the In Vitro Expansion of Endocrine Cells.

In still another embodiment, this invention provides kits for culturing differentiated endocrine cells using the methods described herein. The kits include a container containing one or more PI3K inhibitors. The assay kits can additionally include any of the other components described herein for the practice of the assays of this invention. Such components include, but are not limited to culture media, buffers, selection antibiotics, and the like. The kits may optionally include instructional materials containing directions (i.e., protocols) disclosing the use of PI3K inhibitors for culturing cell that differentiate and show endocrine activity. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Phosphatidylinositol 3-Kinase is a Negative Regulator of Cellular Differentiation The identification of mechanisms involved in the formation and function of the mammalian endocrine system is one of the most important issues in developmental biology. The differentiation and growth of endocrine organs can be regulated at several levels. One level is the regulation of reactions controlled by intracellular signal messengers. This type of regulation provides a different gene expression response to various external stimuli, which is critical for rates of hormone biosynthesis and release. Phosphatidylinositol 3 kinase (PI3K)l is a ubiquitous enzyme that has been shown to be an important mediator of intracellular signaling in mammalian cells. To date, the expanding family of mammalian PI3K consists of three members, each containing a different p110 catalytic subunit (Hiles et al. (1992) *Cell*. 70:419–429, Hu et al. (1993) *Mol. Cell. Biol*. 13:7677–7688. Stoyanov et al. (1995), *Science* 269:690–693). Upon activation, PI3K phosphorylates inositides at the D3 position of the inositol ring to generate such lipid messengers as: PtdIns(3)P, PtdIns(3,4)P2, and PtdIns(3,4,5)P3.

The exact role and downstream molecular targets of these lipid products are unknown. However, it is known that overall increases in the levels of these messengers correlates with mitogenic signaling by growth factors (Cantley et al. (1991) *Cell*. 64:281–302), secretion, and vesicle trafficking (Brown et al. (1995) *J. Cell Biol*. 130:781–796), as well as chemotaxis, cell shape changes, and membrane ruffling (Traynor-Kaplan et al. (1988) *Nature (Lond.)*. 334:353–356; Eberle et al. (1990) *J. Biol. Chem*. 265:16725–16728; Wennstrom et al. (1994) *Oncogene*. 9:651–660). PI3K was reported to be important for the regulation of insulin receptor induced intracellular pathways, including glucose transport (Backer et al. (1993) *J. Biol. Chem*. 268:8204–8212). Similarly, members of the seven transmembrane spanning receptor family, hormone and sensory receptor system in mammalian cells, were recently shown to use PI3K to transduce signals to the interior of the cell and to assemble the ras activation complex (Ptasznik et al. (1995) *J. Biol. Chem*. 270:19969–19973; Ptasznik et al. (1996) *J. Biol. Chem*. 271:25204–25207; Touhara et al. (1995) *Proc. Natl. Acad. Sci. USA*. 92: 9284–9287). Several studies have shown that the PI3K lipid products are signaling intermediates in the induction of cellular differentiation of PC12 pheochromocytoma cells (Hempstead et al. (1992) *Neuron*. 9:883–896; Kimura et al. (1994) *J. Biol. Chem*. 269:18961–18967) as well as of adipocytic 3T3F442A cells (Saad et al. (1994) *Mol Endocrinol*. 8:545–557), suggesting that this enzyme may function as a positive regulator of cellular differentiation in these cell lines.

While the process of endocrine cell differentiation has been extensively studied, no specific intracellular signaling pathway directly involved in regulating expression of endocrine specific genes has been identified. Because of the role of PI3K in mitogenesis, differentiation, and stimulussecretion pathways, we have investigated the possibility that this enzyme regulates endocrine differentiation in mammalian cells. Until recently, most of the studies addressing the role of PI3K in cellular proliferation and differentiation were undertaken using a variety of cell lines and transfection methodologies. Such transformed cells are capable of indefinite replication in culture and express only some of the differentiated properties of their cell of origin. Thus, these approaches provide only limited information about the potential link between PI3K activity and development. With the identification of the drugs wortmannin (Powis et al. (1994) *Cancer Res.* 54:2419–2423) and Ly294002 (Vlahos et al. (1994) *J. Biol. Chem.* 269:5241–5248) as potent PI3K inhibitors, it became possible to directly inhibit the endogenous PI3K activity in cultured primary cells. In the present experiments, we have used, as a model for endocrine differentiation, human fetal-derived pancreatic cells, growing in vitro as islet-like cell clusters (ICCs) (Sandler et al. (1989) *Diabetes*. 38(Suppl1):168–171). The cellular composition of ICCs consists mostly of undifferentiated epithelial cells (z80%) containing putative precursors of the hormone-producing cells (Sandler et al. (1989) *Diabetes*. 38(Suppl 1): 168–171; Otonkoski et al. (1993) *J. Clin. Invest.* 92:1459–1466; Beattie et al. (1994) *J. Clin. Endocrinol. Metab.* 78:1232–1240).

Endocrine cells developing in vitro within ICCs originate from undifferentiated, pluripotent epithelial cells and contain insulin-producing β cells and the three other cell types, a, d, and pp, secreting glucagon, somatostatin, and pancreatic polypeptide, respectively. An advantage of this model system is the ability to mimic steps of the differentiation process in cell culture, as evidenced by the fact that after being transplanted into athymic nude mice, ICCs develop into morphologically and functionally mature endocrine tissue (Sandler et al. (1985) *Diabetes*. 34:1113–1119; Beattie et al. (1994) *J. Clin. Endocrinol. Metab.* 78:1232–1240). We now report that wortmannin or Ly294002 blockade of PI3K activity significantly increased the number of hormone producing cells growing in ICCs. These unexpected results indicate that PI3K plays a role as a negative regulator of cellular differentiation during fetal neogenesis of endocrine system.

MATERIALS AND METHODS

Tissue Culture

The use of human fetal tissue for these studies was reviewed and approved by the Institutional Review Board at our university. Human fetal pancreases at 18–24 gestational wk were obtained with appropriate permissions and patient consent through nonprofit organ procurement programs (Advanced Bioscience Resources, Oakland, Calif.; Anatomic Gift Foundation, Laurel, Md.). Experiments were started by the enzymatic digestion with collagenase P (Boehringer Mannheim Corp., Indianapolis, Ind.) of the human fetal pancreases followed by tissue culture for 5 d, which led to the formation in vitro of ICCs, as previously described in detail (Otonkoski et al. (1993) *J. Clin. Invest.* 92:1459–1466). The cells, cultured for 5 d, were treated continuously with 10 μM Ly294002 (Calbiochem Corp., La Jolla, Calif.), 100 nM wortmannin (Sigma Chemical Co., St. Louis, Mo.), 10 mM nicotinamide (NIC) (Sigma Chemical Co.), or 25 ng/ml hepatocyte growth factor/scatter factor (HGF/SF) (a kind gift of J. S. Rubin, National Cancer Institute, Bethesda, Md.).

These concentrations of wortmannin and Ly294002 were found to be effective in inhibiting PI3K activity in our preliminary, dose-response experiments. The effective doses for NIC and HGF/SF as modulators of endocrine differentiation in fetal islet cells were established in our laboratory previously (Otonkoski et al. (1993) *J. Clin. Invest.* 92:1459–1466; Beattie et al. (1996) *Diabetes.* 45:1223–1228).

PI3K inhibitors, NIC, or HGF/SF were added to the culture medium from the very beginning. Medium plus factor was changed every day for 5 d. For direct comparison, portions of the same pancreases were grown, treated with factors, and used for transcriptional analyses, insulin content and secretion, PI3K activities, and DNA synthesis.

Isolation of Fetal Pancreatic Islets

Effects of PI3K inhibitors on endocrine function were tested not only in ICCs, but also in purified islets. Undifferentiated epithelial cells account for z75–80% of the total cell mass in ICCs. By contrast, purified fetal islets contain about 10 fold fewer undifferentiated epithelial cells (Beattie et al. (1996) *Diabetes.* 46:244–248). Purification of human fetal pancreatic islets was performed as recently described (Beattie et al. (1996) *Diabetes.* 46:244–248). Fetal islets, identified as homogeneous differentiated clusters of dithizonepositive cells, were incubated with factors as above.

RNA Isolation and Analysis

Transcriptional analyses on total RNA (0.5 mg) were performed using a multiprobe ribonuclease protection assay, as previously described (Otonkoski et al. (1993) *J. Clin. Invest.* 92:1459–1466). The housekeeping gene cyclophilin was used as an internal control, and yeast tRNA (10 μM) was included as a negative control. Probes used were of human origin and were described previously (Otonkoski et al. (1993) *J. Clin. Invest.* 92:1459–1466). Target RNAs were quantitated in autoradiographs by scanning densitometry (LKB UltroScan XL Laser) and integrated using Gel Scan XL software (Pharmacia LKB Biotechnology, Inc., Piscataway, N.J.). The probe-specific mRNA signals were normalized to the cyclophilin signal in each sample to account for differences in sample loading between lanes.

Insulin Content, Insulin Secretion, and DNA Synthesis

After incubation with various factors in culture, the ICCs were harvested, and measurements of insulin content, insulin release in response to glucose plus theophylline, and [$^3$H]thymidine incorporation into DNA were performed as described previously (Otonkoski et al. (1993) *J. Clin. Invest.* 92:1459–1466).

PI3K Assay

Aliquots of cell lysates normalized for protein content were incubated for 3 h with antiPI3K antibodies directed against the 85kD regulatory subunit or with antiphosphotyrosine antibodies (Upstate Biotechnology, Inc., Lake Placid, N.Y.). The immune complexes were absorbed onto protein A-Sepharose and washed as described (Ptasznik et al. (1995) *J. Biol. Chem.* 270:19969–19973). PI3K assays were performed directly on beads. Briefly, the reaction was carried out for 10 min in a buffer containing 40 mM Hepes, pH 7.2, 6 mM MgCl$_2$, 1 mM EDTA, 10 mg of PI (Avanti Polar Lipids, Alabaster, Ala.), 10 mM ATP, and 10 mCi [γ$^{32}$P]ATP (6,000 Ci/mmol; DuPont/NEN, Wilmington, Del.). Adenosine (0.2 mM) was added to the reaction mixture to inhibit residual PI 4 kinase activity. After the incubation, the reaction was stopped with methanol plus 2.4 N HCl (1:1, vol/vol), and lipids were extracted, analyzed by thin-layer chromatography, and quantified as described previously (Ptasznik et al. (1995) *J. Biol. Chem.* 270:19969–19973). In some experiments, the direct binding of PI3K to p190Met after HGF/SF stimulation of islet cells was determined, as previously described in detail (Graziani, et al. (1991) *J. Biol. Chem.* 266:22087–22090).

Determination of Total Cellular PIP3

The ICCs, which were pretreated for 5 d with PI3K inhibitors, NIC, HGF/SF, or control buffer, were subsequently harvested and suspended at a concentration of 2 3 10 5 cells/ml in buffer A (30 mM Hepes, pH 7.2, 110 mM NaCl, 10 mM KCl, 1 mM $MgCl_2$, 10 mM glucose), and 1 mCi/ml [$^{32}$P]orthophosphate (HCl-free; DuPont/NEN) was added. The cells were incubated at 37° C. for 2 h and then washed 3× with buffer A. Depending on the type of experiment, the labeled islet cells were either directly lysed by addition of 3 ml chloroform/methanol (1:2, vol/vol), followed by 4 ml chloroform/2.4 M HCl (1: 1, vol/vol) (to measure basal levels of PIP3 ), or labeled cells were first stimulated with 25 ng/ml HGF/SF for the indicated times, and subsequently the reaction was stopped as above (to measure the inducible levels of PIP3 ). Phospholipids were extracted and analyzed by thinlayer chromatography, and the total cellular PIP3 was quantified, as we described previously in detail (Ptasznik et al. (1996) *J. Biol. Chem.* 271 :25204–25207).

Triple Immunofluorescence and Confocal Microscopy

ICCs cultured for 5 d in either control medium or medium containing 10 μM Ly 294002 were paraffin embedded, and 5 mm sections were stained for hormone immunoreactivity. To simultaneously identify cells producing insulin, glucagon, somatostatin, and pancreatic polypeptide (pp), we followed a modification of our previous protocol for multiple labeling (Otonkoski et al. (1996) *J. Clin. Invest.* 79:351–358). Briefly, sections were incubated for 1 h at room temperature with a mixture of primary antibodies: IgG fraction of a sheep anti-human insulin antiserum (The Binding Site, Birmingham, England) (5 mg/ml), mouse monoclonal anti-human glucagon (Sigma Chemical Co.) (1 mg/ml), rabbit anti-human somatostatin antiserum (Dako Corporation, Carpinteria, Calif.) (used at 1:100 dilution), and rabbit anti-human pp antiserum (Chemicon International, Inc., Temecula, Calif.) (used at 1:100 dilution). In separate sections, a mixture of normal sheep, rabbit, and mouse IgGs was used as control reference for specificity of primary antibodies. After washings in PBSDS (5 mM glycine, 0.2% donkey serum, 0.1% BSA), sections were incubated for 1 h at room temperature with a cocktail of F(ab')$_2$ fractions from secondary antibodies: lissamine-rhodamine-conjugated affinity-purified donkey anti-sheep IgGs (5 mg/ml); FITC-conjugated affinity-purified donkey anti-rabbit IgGs (5 mg/ml); and indodicarbocyanine-conjugated affinity-purified donkey anti-mouse IgGs (5 mg/ml). All F(ab')$_2$ were preadsorbed on appropriate multiple species to eliminate the possibility of crossreactivity in multiple labeling protocols (Jackson ImmunoResearch Labs, Inc., West Grove, Pa.). The sections were processed as previously described (Otonkoski et al. (1996) *J. Clin. Invest.* 79:351–358) and viewed on a laser scanning confocal microscope (model MRC1024; BioRad Laboratories, Hercules, Calif.).

Morphometric Analysis and Statistics

Sections were prepared from control and Ly294002 treated ICCs from three independent experiments. After immunostaining, confocal images were acquired from 57 control and 61 Ly294002 treated ICC sections. All images collected (one image per section) were then analyzed for total surface area and insulin, glucagon, somatostatin, and positive cell surface area by using measurement tools in the software NIH Image 1.60 (National Institutes of Health, Bethesda, Md.). Data were analyzed in Stat View 4.01 (Abacus Concepts, Inc., Berkeley, Calif.) for calculation of mean, standard deviation, and parametric statistic (t test).

RESULTS

Figure 7:
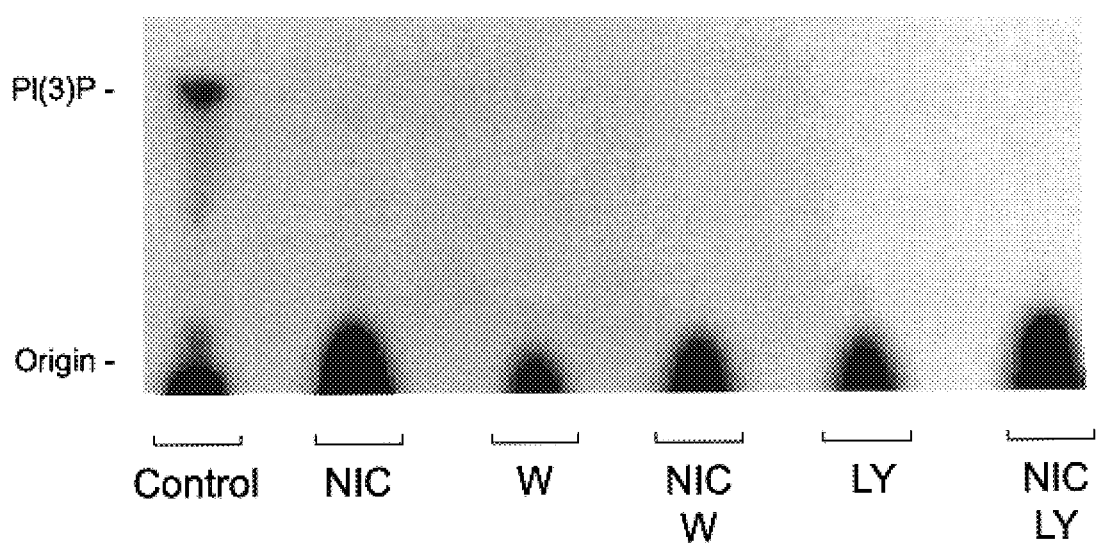
FIG. 7 illustrates the effect of continuous treatment for 5 d with NIC, wortmannin, or Ly294002 on cellular PI3K activity in fetal ICCs. Fetal islet cells were incubated for 5 d with control medium (Control), 10 mM nicotinamide (NIC), 100 nM wortmannin (W), 10 µM Ly294002 (Ly) or combined NIC plus inhibitor. PI3K activity in p85 precipitates from islet cells was analyzed as de-scribed in Materials and Methods. Results shown are representative of two independent experiments.

Inhibition of PI3K Increases Islet-specific Hormone Biosynthesis and Hormone Secretion in Developing Fetal Pancreatic Cells To investigate whether PI3K activation is important for endocrine differentiation of human fetal pancreatic cells, we continuously treated ICCs for 5 d with 100 nM wortmannin or 10 μM Ly294002, concentrations that block over 90% of total PI3K activity in intact fetal islet cells (data not shown; see FIG. 7). We established that these concentrations of wortmannin and Ly294002 almost completely inhibited the rise in PIP3 formation stimulated by growth factors in intact [$^{32}$P]orthophosphatelabeled islet cells. By contrast, these concentrations of inhibitors did not affect significantly the ratio of [$^{32}$P]PIP2 to [$^{32}$P]PIP and [$^{32}$P]PIP to [$^{32}$P]PI in phospholipid labeling experiments where PIP3 levels were measured, implying that other kinases (PI5K and PI4K) were not inhibited under these conditions. Wortmannin, a fungal metabolite, functions as a covalent inhibitor of the catalytic p110 subunits of PI3Ks at nanomolar concentrations, whereas Ly294002, a structurally and mechanistically distinct compound, functions as a noncovalent, competitive inhibitor of PI3Ks at 100 fold higher concentrations than wortmannin (Okada et al. (1994) *J. Biol. Chem.* 269:3563–3567; Powis et al. (1994) *Cancer Res.* 54:2419–2423; Vlahos et al. (1994) *J. Biol. Chem.* 269:5241–5248; Wymann et al. (1996) *Mol. Cell. Biol.* 16:1722–1733).

Figure 1B:
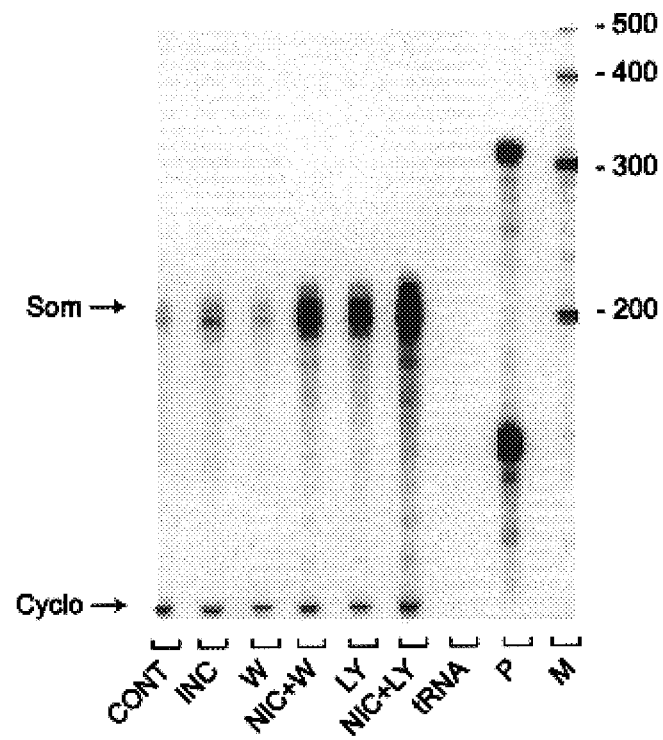

At nanomolar concentrations, wortmannin is thought to be selective for PI3K. Ly294002, even at micromolar concentrations, is quite specific for PI3K and does not affect PI4 K or a number of intracellular Ser/Thr and Tyr kinases (Vlahos et al. (1994) *J. Biol. Chem.* 269:5241–5248). Finally, we have also shown that continuous treatment for 5 d with 100 nM wortmannin 10 μM Ly294002 does not cause notable cytotoxity nor induce apoptosis in fetal pancreatic cells growing as islet-like cell clusters. We measured the transcriptional expression of islet-specific hormone genes in ICCs growing for 5 d in the presence of PI3K inhibitors. As shown in FIG. 1, wortmannin and Ly294002 increased the transcriptional levels of insulin, glucagon, and somatostatin in cells within the ICCs. The pattern of alterations of mRNA levels was strikingly similar to that of insulin protein (see below). Therefore, these data indicate that two structurally distinct compounds have similar effects on hormone transcription as a consequence of their shared ability to function as specific inhibitors of PI3K.

Figure 1C:
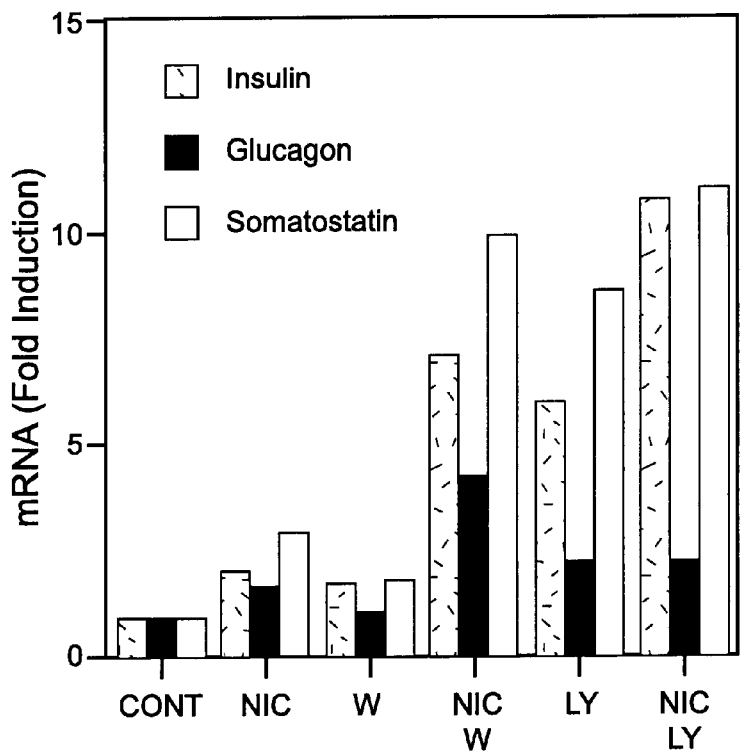

The inhibitors had no effects on cyclophilin mRNA, which was used as an internal control. The quantitative analysis of islet hormone transcription levels, after normalization to cyclophilin expression, is shown in FIG. 1C. To better understand the effect of these PI3K inhibitors on islet hormone gene expression, we compared the effect of PI3K inhibitors alone to the NIC-induced increase in expression of islet-specific hormone genes (Otonkoski et al. (1993) *J. Clin. Invest.* 92:1459–1466). NIC is an inhibitor of the enzyme poly(ADP-ribose) synthetase and can potently induce human fetal islet cell differentiation by influencing the transcription of DNA (Yonemura et al. (1984) *Diabetes.* 33:401405; Sandler et al. (1989) *Diabetes.* 38(Suppl 1): 168–171).

Figure 2A:
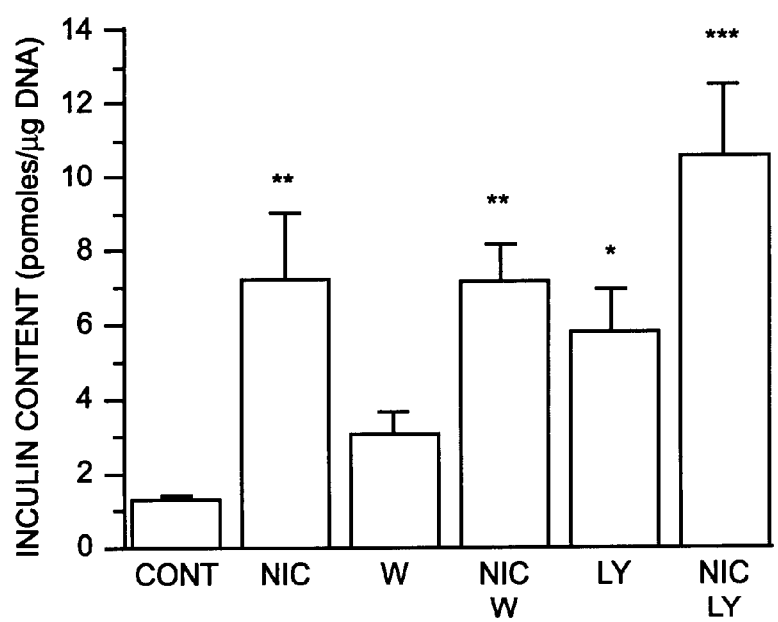
FIGS. 2A and 2B show the stimulatory effects of PI3K inhibitors on insulin content and insulin secretion in fetal islet cells. Replicate groups of 50 human fetal ICCs were cultured for 5 d in the presence or absence of the inhibitors wortmannin (W) or Ly294002 (LY). Nicotinamide (NIC), a potent inducer of endocrine cell differentiation, was also included in some cultures. Insulin content (FIG. 2A) and insulin release (FIG. 2B) were measured. *P<0.05, P<0.005, *P<0.0005; n=8.
Figure 2B:
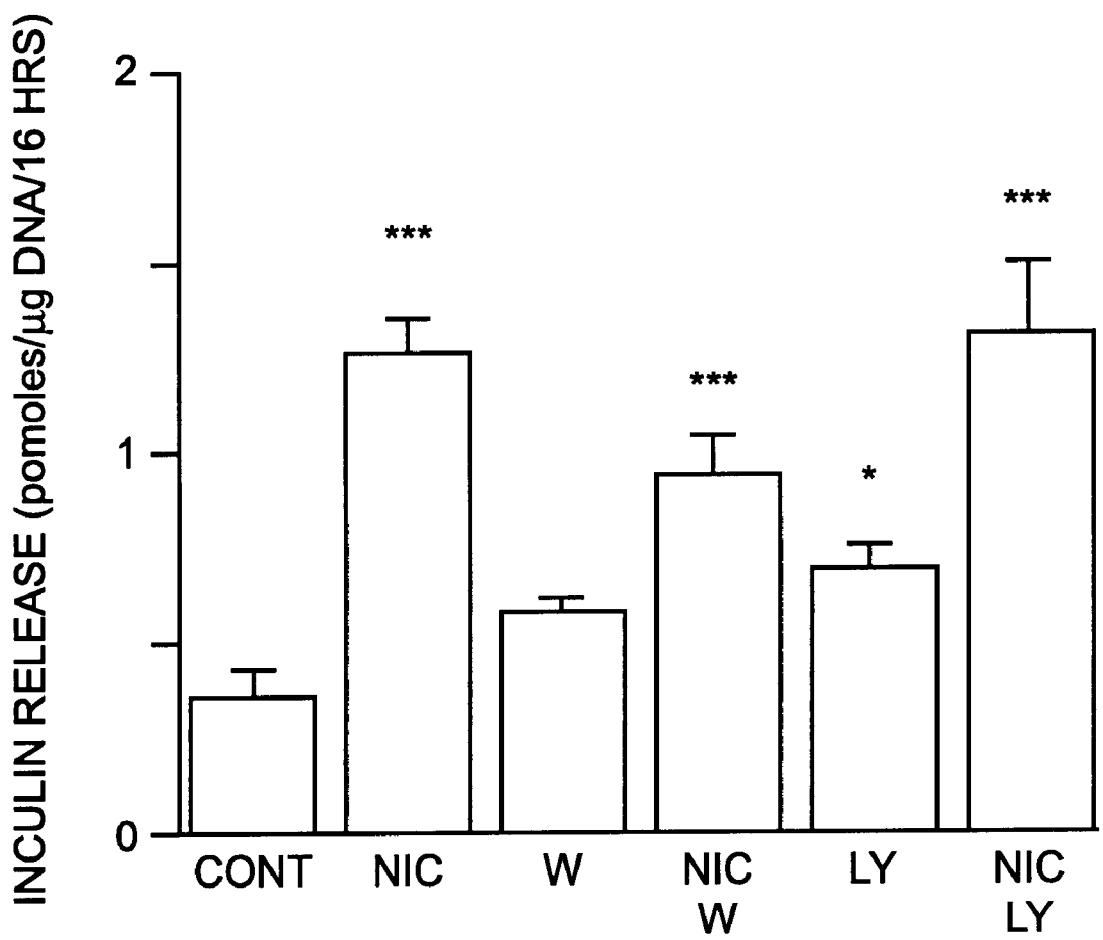

Treatment with the combination of a PI3K inhibitor and NIC resulted in asynergistic increase in mRNA levels of islet-specific hormones (maximum increase is about 10 fold for insulin and somatostatin, and fourfold for glucagon). Taken together, these data suggest that PI3K is a negative regulator of islet-specific gene expression in developing pancreatic cells. We also measured the insulin content and insulin secretion per cellular DNA in fetal ICCs cultured for 5 d in the presence of the PI3K inhibitors. As shown in FIGS. 2A and 2B, we found that both insulin content and secretion were significantly increased in Ly294002 treated cells, as compared to untreated control cells. Wortmannin also induced increases in these parameters, but to a lesser extent. (Wortmannin appears to be a much less stable agent than Ly294002 in culture medium [Kimura et al. (1994 *J. Biol. Chem.* 269:18961–18967].)

The pattern of alterations of insulin secretion was almost identical to that of insulin content, indicating a close functional association between these two parameters. This would suggest that a continuous blockade of PI3K activity could secondarily increase insulin secretion through potent stimulation of insulin biosynthesis in developing islet cells. Consistent with this, we observed no direct effect of PI3K inhibitors on insulin secretion when islet cells were treated with these inhibitors for a short time (0.5 and 2 h). No significant differences were observed in insulin content under these conditions. The observation that short-term inhibition of PI3K does not significantly affect insulin secretion was also recently shown in rat islets and insulin-secreting βTC3 cells and has already been exhaustively discussed by other investigators (Gao et al. (1996) *Diabetes.* 45:854–862). Taken together, these data suggest that the continuous blockade of PI3K activity triggered changes in mRNA levels and that these changes were followed by a significant increase in hormone biosynthesis and a subsequent increase in hormone secretion.

Figure 3:
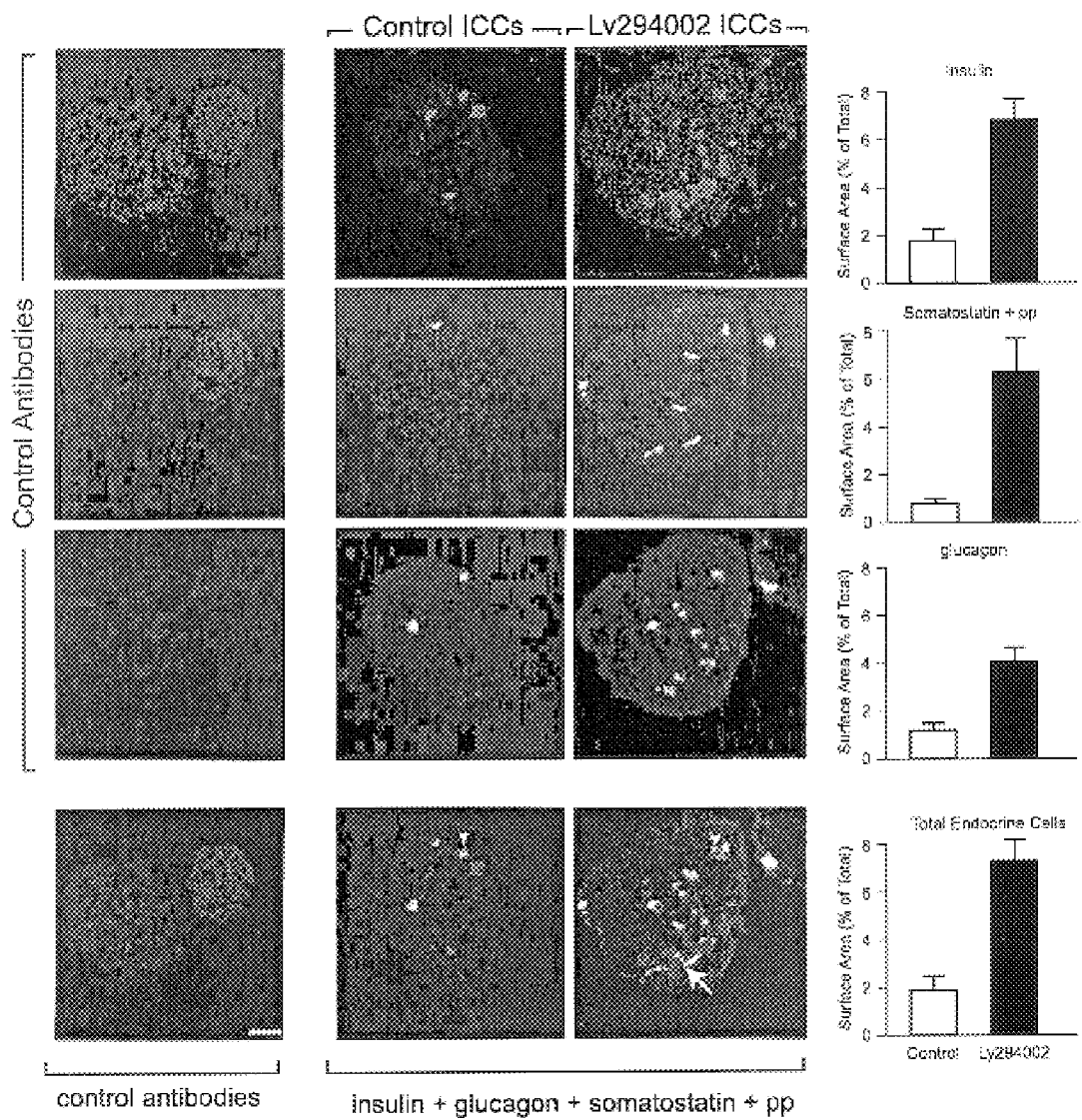
FIG. 3 shows the increased frequency of endocrine-positive cells and endocrine precursors in PI3K inhibitor-treated fetal islet cultures. Representative fields, collected by confocal microscopy, are shown for control and Ly294002 treated ICCs. Immunoreactivity for insulin was visualized in red, somatostatin and pp in green, and glucagon in blue. Bar graphs represent the morphometric analysis of endocrine cell frequency for each hormone and show the immunoreactive surface area expressed as percent of total surface area of ICCs. Notably, the endocrine surface area is significantly increased for all hormones in Ly294002 treated ICCs (insulin, P<0.01; somatostatin and pp, P<0.03; glucagon, P<0.03; n=3). When the three fluorescence spectra are merged (lower panels) to measure the total endocrine cell surface, hormone colocalization can also be appreciated. Insulin and glucagon coexpression is highlighted by the appearance of a purple color (arrowheads) resulting from the overlap of red and blue, whereas colocalization of insulin and somatostatin or pp is shown by the yellow color (arrow) resulting from the overlap of red and green fluorescences. Note that the frequency of cells coexpressing multiple hormones is increased in Ly294002-treated ICCs: seven cells coexpressing insulin and glucagon (purple) and two cells coexpressing insulin and somatostatin or pp (yellow). Morphometric analysis demonstrates that the total endocrine cell surface area is significantly increased in Ly294002-treated ICCs (lower right bar graph). Control sections incubated with irrelevant primary antibodies did not show any detectable immunoreactivity (left panels). Bar, 12 mm.

To determine whether PI3K inhibitors increase the proportion of islet cells expressing hormones, confocal immunofluorescent detection of all islet-specific hormones, followed by morphometric analysis of the ICCs, was carried out. FIG. 3 shows representative fields of a microscopic analysis performed on sections from human fetal ICCs, cultured with or without Ly294002 for 5 d. Only a few hormone positive cells were visible in ICCs cultured in control medium. By contrast, hormone-positive cells were more common in ICCs cultured with the PI3K inhibitor (4.4 fold increase in the total percentage of endocrine-positive cells in Ly294002 treated ICCs, as compared to control ICCs). Interestingly, in Ly294002 treated ICCs, we detected more cells positive for more than one protein, indicating that the PI3K inhibitor can trigger activation of multiple hormone-specific genes in a single cell.

It was previously shown that coexpression of multiple hormones represents an early step in the endocrine differentiation program of islet cell progenitors (Alpert et al. (1988) *Cell.* 53:259–308; Herrera et al. (1991) *Development (Camb.).* 113:1257–1265). The present results thus suggest that PI3K inhibitors induce a process of endocrine differentiation in fetal islet precursor cells.

Inhibition of PI3K Decreases DNA Synthesis in Fetal Pancreatic Cells

Figure 4A:
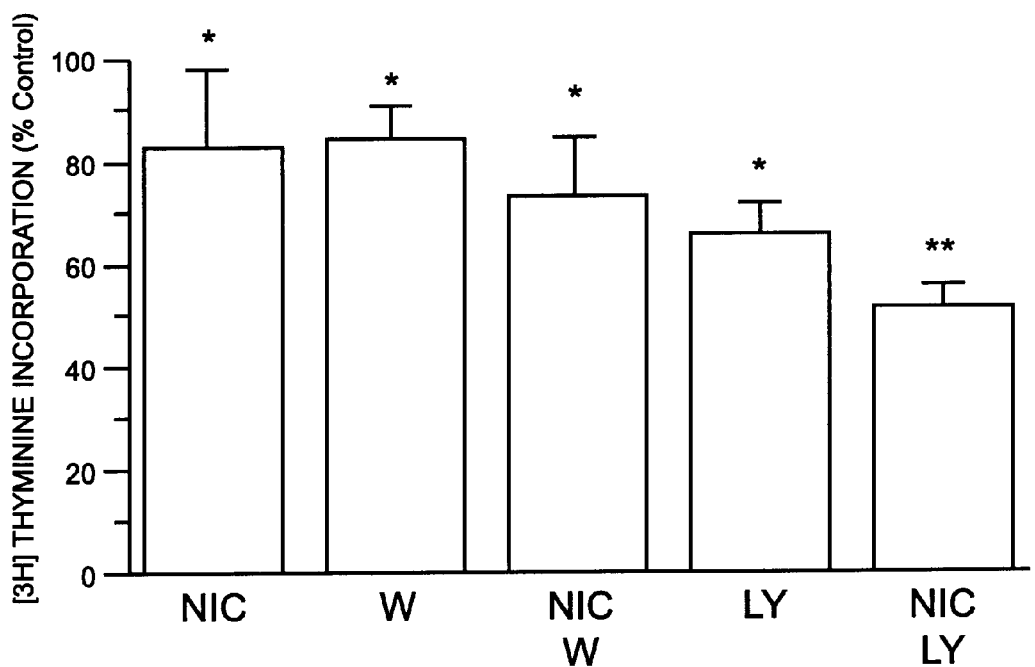
FIGS. 4A, 4B, and 4C show the inhibition of proliferation in fetal islet cells by PI3K inhibitors.
Figure 4B:
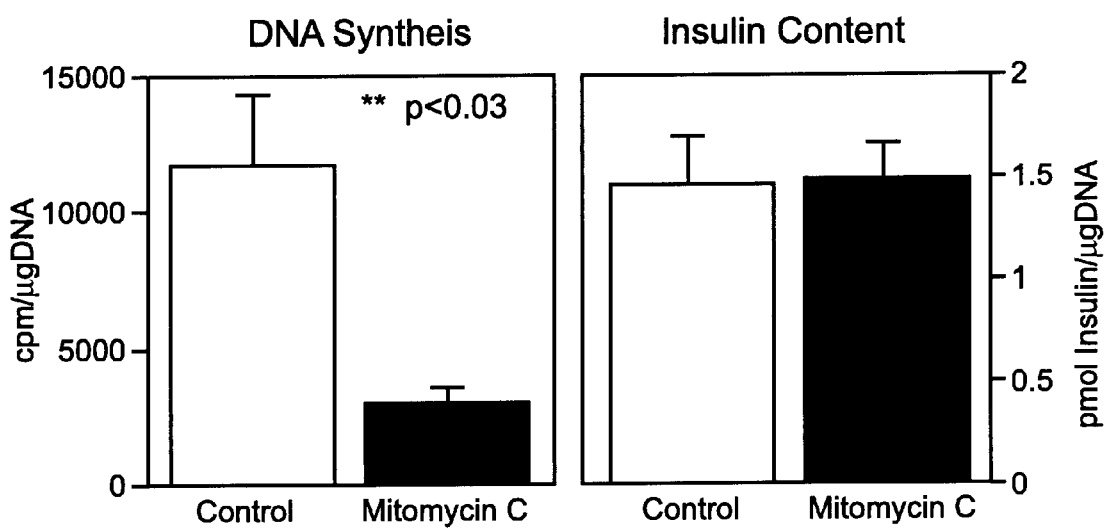
Figure 4C:
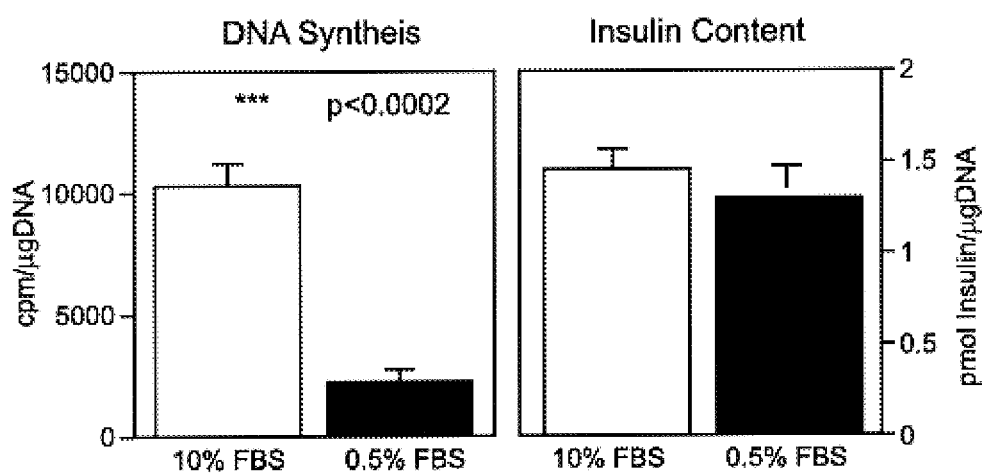

We measured DNA synthesis in fetal ICCs cultured in the presence of the PI3K inhibitors. As shown in FIG. 4A, wortmannin and Ly294002 significantly decreased the [$^3$H] thymidine incorporation into DNA in cells within the ICCs. Treatment with the combination of the PI3K inhibitor and NIC resulted in a synergistic decrease in DNA synthesis. To make certain that the observed increase in islet-specific hormone expression in PI3K inhibitor-treated cells is not secondary to nonspecific blockade of the cell cycle, we measured insulin protein expression in mitomycin C-treated or serum-starved cells. As shown in FIGS. 4B and 4C, neither mitomycin C-induced blockade of DNA synthesis nor serum starvation affected insulin protein expression in ICCs. Consistent with this observation, neither mitomycin C, which is known to interact directly with DNA (Tomasz et al. (1987) *Science (Wash. DC).* 235:1204–1208), nor serum starvation significantly affected basal PI3K activity in fetal islet cells. Thus, the stimulatory effect of PI3K inhibitors on endocrine differentiation is not secondary to blockade of cell proliferation but is due to the specific blockade of PI3K.

Figure 5:
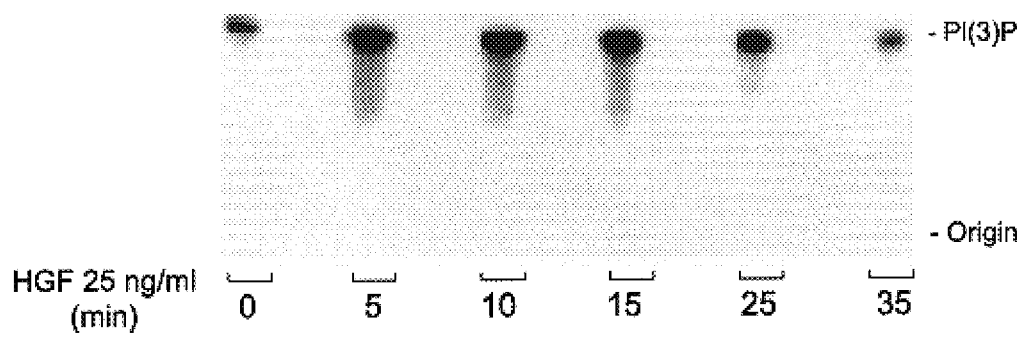
FIG. 5 illustrates HGF/SF-induced increase of PI3K activity in fetal ICCs. ICCs starved for 24 h were stimulated for the indicated times with HGF/SF (25 ng/ml). Equivalent amounts of cell lysates were immunoprecipitated with antiphosphotyrosirie antibody (Upstate Biotechnology, Inc.), and immune complexes were assayed for PI3K activity as described in Materials and Methods. The position of migration of phosphatidylinositol 3 phosphate (PI(3)P) is indicated. Results shown are representative of two independent experiments.
Figure 6A:
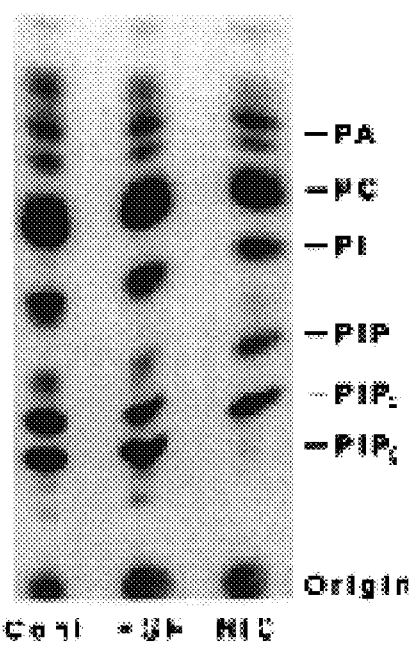
FIGS. 6A and 6B illustrate the effect of continuous treatment for 5 d with HGF/SF or NIC on PIP3 formation in fetal ICCs.
Figure 6B:
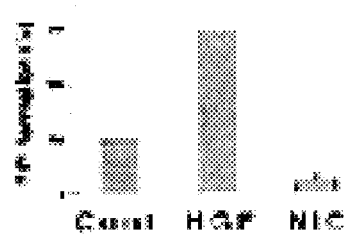

HGF/SF or NIC-dependent Regulation of Endocrine Differentiation is Inversely Related to PI3K Activity To clarify the correlation between PI3K activity and endocrine specific gene expression, we examined whether any of the recently described modulators of endocrine differentiation could participate in regulating PI3K activity in islet cells. Mesenchyme-derived HGF/SF is a physiological modulator of endocrine differentiation in human fetal islet cells. When fetal ICCs were induced to proliferate by the addition of HGF/SF, a marked down-regulation of both insulin and glucagon gene transcription, as well as insulin protein biosynthesis, was observed (Beattie et al. (1996) *Diabetes.* 45:1223–1228; Otonkoski et al. (1996) *J. Clin. Invest.* 79:351–358). By contrast, addition of NIC under the same conditions resulted in an increase in insulin and glucagon mRNA levels and insulin protein biosynthesis. These data indicate a role for HGF/SF in promoting proliferation and inhibiting the endocrine function of fetal islet cells. The HGF/SF receptor is known to function by activating PI3K in a variety of cellular systems (Graziani, et al. (1991) *J. Biol. Chem.* 266:22087–22090). Consistent with this, cellular PI3K is robustly activated in fetal islet cells after acute HGF/SF stimulation, and this activation results from direct binding of PI3K to the HGF/SF receptor (FIG. 5). Similarly, analysis of [$^{32}$P]orthophosphate labeled ICCs, growing continuously in the presence of HGF/SF, showed a threefold increase in levels of the major lipid product of PI3K; PIP3 (FIG. 6).

Thus, the HGF/SF-triggered down-regulation of hormone-specific genes is associated with an increase in proliferation of islet cells and with an increase of PI3K activity. In contrast to HGF/SF, NIC is known to increase both insulin content and insulin release in ICCs (Sandler et al. (1989) *Diabetes.* 38(Suppl1): 168–171), as well as to upregulate the expression of islet-specific hormone genes (Otonkoski et al. (1993) *J. Clin. Invest.* 92:1459–1466).

FIG. 7 shows the amount of PI3K activity measured in p85 subunit antibody immunoprecipitates from control, NIC-treated, and PI3K inhibitor-treated fetal ICCs. A significantly lower (about fivefold) amount of PI3K activity was present in p85 immunoprecipitates from NIC-treated cells, as compared to untreated cells. We consistently observed that the basal level of PIP3 was significantly lower in NIC-treated ICCs than in control cells (FIG. 6). Treatment with wortmannin or Ly294002 eliminated 90% of control PI3K activity under these conditions (FIG. 7).

Inducibility of cellular PI3K activity by growth factors, as well as the de novo formation of PIP3, was significantly reduced in NIC-treated cells. There was no change in the actual level of p85 protein during NIC treatment, as determined by Western blotting, nor was there a direct inhibitory effect of various concentrations of NIC on PI3K activity in vitro in p85 immunoprecipitates, indicating that NIC is not a direct inhibitor of PI3K.

The mechanism by which NIC attenuates cellular PI3K activity in developing fetal islet cells remains to be determined. The cell culture and treatment conditions used in FIG. 7 were identical to those used in FIGS. 1 and 2, indicating that an inverse correlation exists between the amount of PI3K activity and the stage of endocrine maturity in islet cells during fetal neogenesis.

DISCUSSION

The cellular signaling pathways that are required for endocrine differentiation are unknown. The present studies clearly indicate that lipid products of PI3K are an important part of the regulatory network that links differentiation signals at the cell surface of endocrine precursors to transcriptional responses in the nucleus. We demonstrate a previously unrecognized function for PI3K-as a negative regulator of endocrine differentiation in developing mammalian cells. Blockade of PI3K activity in primary cultured fetal pancreatic cells resulted in a robust activation of endocrine differentiation. Treatment of ICCs with PI3K inhibitors increased transcription of islet-specific hormone genes, expression of islet-specific hormone proteins, insulin content, insulin release in response to secretagogues, the total number of endocrine-positive cells developing in islets, and the number of precursor islet cells coexpressing multiple hormones. By contrast, DNA synthesis was significantly decreased in the PI3K inhibitor-treated islet cells, as compared to untreated cells. However, inhibition of DNA synthesis by serum starvation or by treatment with cell cycle-blocking antibiotics had no effect on islet-specific hormone expression. This implies that the observed effects are not secondary to nonspecific blockade of the cell cycle, but they can be attributed directly to specific inhibition of PI3K. As a further indication of the involvement of PI3K in regulating endocrine differentiation, we also observed that the activity of this enzyme was inversely correlated with the HGF/SF-induced downregulation or NIC-induced upregulation of islet-specific hormone gene expression, providing support for the role of PI3K as a negative regulator of endocrine differentiation.

The basis for the interaction of cytoplasmic phospholipid messengers with transcriptional factors in the nucleus is, at present, unknown. Only a few potential biochemical targets of phosphoinositides have been found in mammalian cells (for review see Carpenter and Cantley (1996) *Curr. Opin. Cell Biol.* 8:153–158). The exact role and immediate downstream molecular targets of PtdIns(3,4)P2 and PtdIns(3,4,5) P3 have not been identified. This is accurate for all known cellular functions of PI3K in various systems. Thus, the precise molecular mechanisms that link the inhibition of the PI3K to the induction of endocrine differentiation remain to be elucidated.

It has been reported that proteins of the jun family can inhibit islet-specific hormone gene transcription both in vivo (Inagaki et al. (1992) *Proc. Natl. Acad. Sci. USA.* 89:1045–1049) and in vitro (Henderson and Stein (1994) *Mol. Cell. Biol.* 14:655–662). The jun transcription factors block activity of these genes through the Ebox elements, which are common for insulin, glucagon, and somatostatin (Kruse et al. (1993) *Genes Dev.* 7:774–786; Cordier-Bussat et al. (1995) *Mol. Cell. Biol.* 15:3904–3916). The known ability of PI3K to activate ras and subsequently the MAP-KJun cascade (Pulverer et al. (1991) *Nature (Lond.)* 353:670–672; Thomas et al. (1992) *Cell.* 68:1031–1036; Hu et al. (1993) *Mol. Cell. Biol.* 13:7677–7688) provides a potentially direct link between PI3K signaling and the inhibition of islet-specific hormone gene expression. This scenario would explain why treatment with PI3K inhibitors can release the blockade of all islet-specific hormone genes, which is described in the present experiments.

Alternatively, it is possible that the functional association of PI3K with the islet-specific hormone genes is mediated by protein kinase C (PKC)dependent pathways. Several recent reports have indicated that PI3K might activate PKC isoforms both in vitro and in vivo (Nakanishi et al. (1993 *J. Biol. Chem.* 268:13–16; Toker, et al. (1 994) *J. Biol. Chem.* 269:32358–32367). PKC-dependent branches of signal transduction pathways are known as upstream regulators of several regulatory genes and transcription factors, including members of the crel family (NFkB), as well as members of the fos/jun family involving AP1 sites (Leonardo and Baltimore (1989) *Cell.* 58:227–229; De Tata et al. (1993) *Exp. Cell. Res.* 205:261–269). PKC was previously suggested to be involved in intracellular control of insulin anabolism and secretion (for review see Newgard et al. (1995) *Annu. Rev. Biochem.* 64:689–719). Thus, the PI3K could modify islet-specific gene expression in a PKC-dependent manner.

Another explanation for our results would have to imply that PI3K can control biosynthesis of transcriptional factors for hormone gene expression during fetal neogenesis. We have recently shown that phosphoinositides may regulate the expression of islet/duodenum homeobox1 (IDX1) transcriptional factor in undifferentiated rat insulinoma cells growing in vitro at low passages. IDX1 (PDX1, IPF1, STF 1) is known to be important for activation of islet-specific genes and development of endocrine pancreas (Josson et al. (1994) *Nature (Lond.)* 371 :606–609; Miller (1994) *EMBO (Eur. Mol. Biol. Organ.) J.* 13:1145–1156; Watada et al. (1996) *Diabetes.* 45:1826–1831). Experiments to test this alternative in primary growing human fetal cells are in progress. The data presented here strongly suggest that the functional association between PI3K activity and islet-specific gene expression is part of a more general developmental program that coordinates cell differentiation and cell division.

It has previously been suggested that the general function of HGF/SF is to allow various epithelial cells to rearrange during embryogenesis by promoting their proliferation, scattering, and invasiveness (Brinkmann et al. (1995) *J. Cell Biol.* 13 1:1573–1586). The ability of PI3K to inhibit islet-specific hormone gene expression, which we show in our present experiments, provides an explanation for the link between the activation of the HGF/SF receptor and the downregulation of islet-specific gene transcription. Since PI3K is activated in islet cells by HGF/SF (FIGS. 5 and 6), it could serve in these proliferating cells at the same time to block insulin synthesis and secretion.

We have clearly shown that induction of endocrine differentiation by PI3K inhibitors is associated with a decrease in DNA synthesis in ICCs (FIGS. 1, 2, 3, 4) and, vice versa, that the transition of fetal ICCs towards proliferation, by the addition of HGF/SF, is associated with downregulation of islet-specific hormone gene expression and a decrease in the hormone protein content (Beattie et al. (1996) *Diabetes.* 45:1223–1228; Otonkoski et al. (1996) *J. Clin. Invest.* 79:351–358). Thus, according to our present results, it is possible to suggest that PI3K may functionally convert activation of growth factor receptors into downregulation of tissue-specific genes, and in this way accommodate the rates of differentiation versus proliferation in developing tissues. Thus, cell differentiation and cell division would be modulated in a coordinated way, by the common signaling transducer PI3K.

An inverse relationship between proliferation and endocrine differentiation in insulin-producing cells has already been demonstrated previously (Philippe et al. (1987 a) *J. Clin. Invest.* 79:351–358; Pilippe et al. (1987 b) *Mol. Cell Biol.* 7:560–563; Oberg et al. (1994) *Growth Fact.* 10:115–126). Our observation is also in agreement with the general view that tissue-specific functions inversely correlate with cellular growth during embryogenesis.

It is known that external stimulation of islet cells with insulin inhibits insulin gene expression in these cells (Koranyi et al. (1992) *J. Clin. Invest.* 89:432436). Consistent with our present results, it is possible to suggest that PI3K, which is known to be a downstream target for the insulin receptor (Backer et al. (1993) *J. Biol. Chem.* 268:82048212), might functionally link activation of this receptor to down-regulation of insulin and other hormone-specific genes in fetal islet cells. This is also consistent with the recent observation that islet β cells express the insulin receptor mRNA and insulin receptor substrate 1, i.e., the same signal transducers that are known to mediate insulin action in peripheral insulin target tissues (Harbeck et al. (1996) *Diabetes.* 45:711–717). Since PI3K is activated by insulin in target tissues, it could serve in β cells at the same time to block insulin biosynthesis and secretion. An autocrine feedback loop acting through PI3K would be part of the signaling mechanism maintaining homeostatic control within developing fetal cells. It has been shown that during development, multipotential epithelial stem cells give rise to all islet cell phenotypes (Teitelman et al. (1987) *Dev. Biol.* 121:454–466; Alpert et al. (1988) *Cell.* 53:259–308). The double control mechanism was suggested to be necessary during islet development (Alpert et al. (1988) *Cell.* 53:259–308; Herrera et al. (1991) *Development* (Camb.). 113:1257–1265; Cordier-Bussat et al. (1995) *Mol. Cell. Biol.* 15:3904–3916). The first step occurs when all the islet-specific hormone genes are activated, and the cells are able to coexpress multiple hormone genes. The second step occurs when the differentiating cells become restricted to express only one hormone gene. The data presented here strongly point to the early islet progenitor cells as a target, which responded to our treatment with PI3K inhibitors. Thus, we observed that treatment with these inhibitors released the blockade of all hormone genes in undifferentiated pancreatic cells and significantly increased the number of cells coexpressing multiple hormone proteins, which are known to represent precursors of terminally differentiated islet cells. As a further indication of the involvement of progenitor islet cells, we also observed that the PI3K inhibitors combined with NIC caused the synergistic increase of the mRNA levels of islet specific hormone genes. NIC alone was previously shown to induce these mRNA levels only in precursor cells, without any effect on mature endocrine islet cells (Otonkoski et al. (1993) *J. Clin. Invest.* 92:1459–1466). Finally, we observed no effect of PI3K inhibitors or NIC on endocrine function in purified fetal islets. These results would suggest, again, that the effects that we found in primary cultured ICCs, rich in precursor cells, were developmentally dependent. For this reason, these effects cannot be detected in purified islets, which contain mostly terminally differentiated endocrine cells and few precursor cells (see Materials and Methods).

In conclusion, our results describe a role of PI3K in regulating development of the human endocrine system. Interestingly, it was shown just recently that inhibition of the PI3K displays a stimulatory effect on melanogenesis and dendrite outgrowth in B16 murine melanoma cell line (Busca et al. (1996) *J. Biol. Chem.* 271:31824–31830). Thus, the negative regulation of cellular differentiation by PI3K, which we independently discovered in primary growing human cells during fetal neogenesis, may be a general phenomenon. Nevertheless, other authors have previously shown a positive involvement of PI3K in PC12 pheochromocytoma and 3T3 F442 A adipocytic cell lines differentiation (Hempstead et al. (1992) *Neuron.* 9:883–896; Kimura et al. (1994) *J. Biol. Chem.* 269:18961–18967; Saad et al. (1994) *Mol. Endocrinol.* 8:545–557). Taken together, all available results suggest that the PI3K may play a dual role as both a positive and negative regulator of cellular differentiation in mammalian cells. Future studies directed at the downstream signaling elements coupled to PI3K should prove informative, as will further investigation of the transcriptional factors by which PI3K links to tissue-specific gene regulation.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of inducing differentiation of endocrine cells, said method comprising culturing a mammalian endocrine precursor cell in the presence of a phosphatidylinositol 3-kinase (PI3K) inhibitor whereby said endocrine precursor cell differentiates into a cell having endocrine activity.

2. The method of claim 1, wherein said phosphatidylinositol 3-kinase inhibitor is selected from the group conisiting of wortmannin, a wortmannin analogue, Ly294002, and a Ly294002 analogue.

3. The method of claim 1, wherein said phosphatidylinositol 3-kinase inhibitor is wortmannin.

4. The method of claim 1, wherein said phosphatidylinositol 3-kinase inhibitor is Ly294002.

5. The method of claim 1, wherein said mammalian precursor cell is a precursor cell from a pancreas.

6. The method of claim 5, wherein said precursor cell is from a human pancreas.

7. The method of claim 6, wherein said human pancreas is a fetal human pancreas.

8. The method of claim 1, wherein said endocrine precursor cell is from an embryonic tissue.

* * * * *